United States Patent [19]
Boime et al.

[11] Patent Number: 5,177,193
[45] Date of Patent: Jan. 5, 1993

[54] MODIFIED FORMS OF REPRODUCTIVE HORMONES

[75] Inventors: Irving Boime; Martin M. Matzuk, both of St. Louis, Mo.

[73] Assignee: Washington University, St. Louis, Mo.

[21] Appl. No.: 532,254

[22] Filed: Jun. 1, 1990

Related U.S. Application Data

[63] Continuation-in-part of Ser. No. 313,646, Feb. 21, 1989.

[51] Int. Cl.$^5$ .............................................. C07K 13/00
[52] U.S. Cl. .................................... 530/397; 530/398
[58] Field of Search ............................... 530/397, 398

[56] References Cited

U.S. PATENT DOCUMENTS 4,923,805  5/1990  Reddy et al. ..................... 435/69.4

FOREIGN PATENT DOCUMENTS 8604589  8/1986  PCT Int'l Appl. .

OTHER PUBLICATIONS

Matzuk et al., *J. of Cell Biol* 109:1429–1438 (1989).
Matzuk et al., *J. Cell Biol.* (1988) 106:1049–1059.
Matzuk et al., *J. Biol. Chem.* (1989) 264(5):2409–2414.
Matzuk et al., *Mol. Endocrinol.* (1988) 2(2):95–100.
Stanley "Molecular Cell Genetics: The Chinese Hamster Ovary Cell" Gottesman ed., J. Wiley & Sons Publisher, New York, (1985) pp. 745–772.
Case et al., *Biology* (1979) Second Edition, Macmillan Publ., Co., New York, p. 455.
Baker et al., *The Study of Biology* (1982) Fourth Edition Addison-Wesley Publ. Co., Ma. pp. 417–419.
Boorstein et al., *Nature* (1982) 300:419–422.
Boothby et al., *J. Biol. Chem.* (1981) 256:5121–5227.
Channing et al., *Endocrinol.* (1978) 103:341–348.
Fiddes et al., *J. Mol. Appl. Genetics* (1981) 1:3–18.
Fiddes et al., *Nature* (1980) 286:684–687.
Glaser et al., *Nature* (1986) 321:882–887.
Hayashizaki et al., *FEBS Letters* (1985) 188:394–400.
Jameson et al., *Mol. Endocrinol.* (1988) 2:806–815.
Jameson et al., *J. Clin. Endocrinol. Metab.* (1986) 64:319–327.
Kalyan et al., *J. Biol. Chem.* (1983) 258:67–74.
Keutmann et al., *Biochem.* (1983) 3067–3072.
Kim et al., *DNA* (1988) 7:277–333.
Matzuk et al., *Proc. Natl. Acad. Sci. USA* (1987) 84:5354–5358.
Maurer et al., *DNA* (1986) 5:363–369.
Morell et al., *J. Biol. Chem.* (1971) 246:1461–1467.
Moyle et al., *J. Biol. Chem.* (1975) 250:9163–9169.
Policastro et al., *J. Biol. Chem.* (1983) 258:11492–11499.
Watkins et al., *DNA* (1987) 6:205–212.
Whitfield et al., "Frontiers in Thyroidology" (1986) Medeiros-Nato et al., editors, pp. 173–176, Plenum Press, New York.
Biome et al., *Adv. Exp. Med. Biol.* (1986) 205:267–280.
Gottlieb et al., *J. Biol. Chem.* (1975) 250(9):3303–3309.

Primary Examiner—David Lacey
Assistant Examiner—Shelly J. Guest
Attorney, Agent, or Firm—Morrison & Foerster

[57] ABSTRACT

The invention provides recombinant native and mutein forms of human reproductive hormones with characteristic glycosylation patterns which are influential in the metabolic activity of the protein. The invention also provides recombinant mutant forms of the human alpha subunit common to FSH, LH, CG, and TSH, to obtain hormones which also have unique glycosylation patterns. Also provided are recombinant materials to produce these subunits separately or together to obtain complete heterodimeric hormones of regulated glycosylation pattern and activity. Modified forms of LH and FSH beta subunits which enhance the rate of dimerization and secretion of the dimers or individual chains are also disclosed.

7 Claims, 15 Drawing Sheets

```
D3
    gcttcaggctagcatggtcatattaatacccacacaaatccacacaaggtgttagttgcacatgattttg TATAAAA ggtga
                                                                            ‾‾‾‾‾‾‾ EXON I
                                                                                ↓
    actgagattcattcagtct  acagctctgccaggcaaggcagccgaccacaggtgagtctggcatctaccgttttcaa
                   ↓    ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
     gtg  gtgacagctactttttgaaattacagattgtcaggacatggaggacaaa...0.7 kb...ttcattgtttgcttccc
    ‾‾‾‾‾ ag accaggATGAAGAGACACTCCAGTTTTTCTTCCTTTTCTGTTGCTGGAAAGCAATCTGCTGCAATAGCTGTGAGCTGACC
          MetLysThrLeuGlnPhePhePheLeuPheCysCysTrpLysAlaIleCysCysAsnSerCysGluLeuThr
          -18                                                                 1
                                                                             EXON II
    AACATCACCATTGCAATAGAAGAAGAATGTCGTTTCTGCATAAGCATCAACACCACTTGGTGTGCTGGCTACTGCTAC
    AsnIleThrIleAlaIleGluLysGluGluCysArgPheCysIleSerIleAsnThrThrTrpCysAlaGlyTyrCysTyr
              10                         20                              30

ACCAGG  gtaggtaccatg....1.35 kb...aaataggaacttccacacaataacctaactctctctcttaaactcctc
    ‾‾‾‾‾‾‾
    ThrArg
```

FIG. 2A ag GATCTGGTGTATAAGGACCCAGGCCCAAATCCAGAAAACATGTACCTTCAAGGAACTGGTATACGAAACAGTG
AspLeuValTyrLysAspProAlaArgProLysIleGlnLysThrCysThrPheLysGluLeuValTyrGluThrVal
    40                          50                          60

EXON III

AGAGTGCCCGGCTGTGTCTCACCATGCAGATTCCTGTATACATACCCAGTGGCCACCAGTGTCACTGTGGCAAGTGTGAC
ArgValProGlyCysAlaHisHisAlaAspSerLeuTyrThrTyrProValAlaThrSerValThrCysGlyLysCysAsp
        70                          80

AGCGGACAGCACTGATTGTACTGTGCGAGGCCTGGGGCCCAGCTACTGCTCCTTTGGTGAAATGAAAGAATAAagatcagtg
SerAspSerThrAspCysThrValArgGlyLeuGlyProSerTyrCysSerPheGlyGluMetLysGlu Term
    90                         100                         110 gacattcaggccacatccctgtcctgaaggaccaagatattcaaaaagtctgtgtgtgcaatgtcccaggggaca aaccactggatcaggggattcagactctctactgatccctggtctactgagagggaactctgggaattgagagtgctgggg .....0.55 kb.....  aaattgtaattgggggctgtggaattagcctgctctctattcattacttaaacaaattgtcac atgctactaggctcctgcaaactcccttttttgagataaaggaaaaaccaaactatctcaccctacccctccctaggatcc
                                                                    └─H1

FIG. 2B

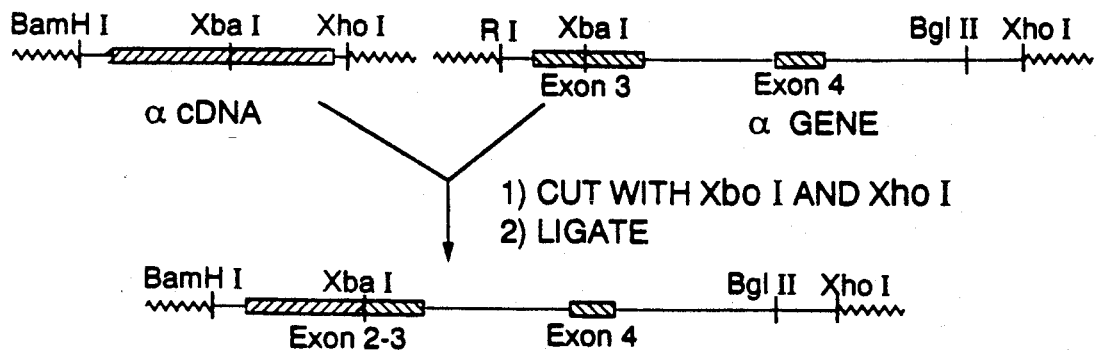
FIG. 3A
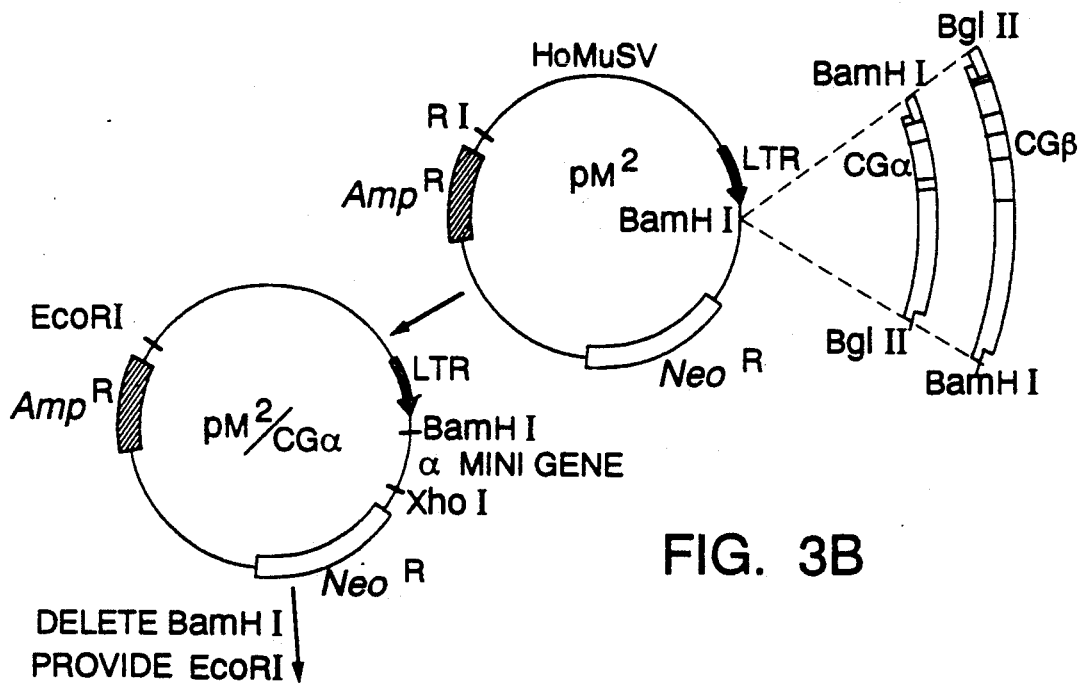
FIG. 3B
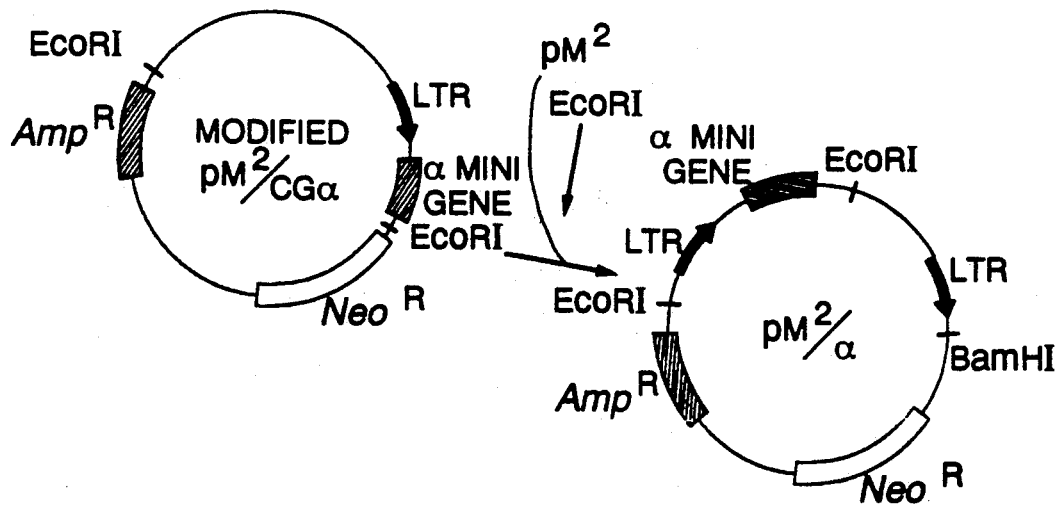

FIG. 6

|    | 1   | 2   |   | 8   | 9 | 10  |   | 13  | 15  | 23 | 26 | 30  | 34 | 38 | 42  |
|----|-----|-----|---|-----|---|-----|---|-----|-----|----|----|-----|----|----|-----|
| LH | ARG | ... |   | TRP | C | HIS |   | ASN | ILE |    |    | ASN |    |    | MET |
| CG | ... | LYS |   | ARG | C | ARG |   | ASN | THR | C  | C  | ASN | C  | C  | THR | intron after position 42 (CG), PvuII site indicated.

|    | 47  | 51  | 57 | 58  | 72 | 77  | 82  | 83  | 88 | 89  | 90 | 91  |
|----|-----|-----|----|-----|----|-----|-----|-----|----|-----|----|-----|
| LH | ALA | PRO | C  | THR | C  | ASP | PHE | PRO | C  | ARG | C  | GLY |
| CG | GLY | ALA | C  | ASN | C  | ASN | TYR | ALA | C  | GLN | C  | ALA |

|    | 92  | 93 | 97  | 100 | 110 | 112 | 114 | 115 | 121 |      |      |      |      |      |      |      | 145 |
|----|-----|----|-----|-----|-----|-----|-----|-----|-----|------|------|------|------|------|------|------|-----|
| LH | PRO | C  | SER | C   |     | C   | HIS | GLN | LEU | SER  | GLY  | LEU  | LEU  | PHE  | LEU  | PRO  | GLN |
| CG | LEU | C  | THR | C   |     | C   | ASP | ARG | PHE | GLN  | ASP  | SER  | SER  | SER  | LYS  | ALA  |     |

F.S. marked at position 115.

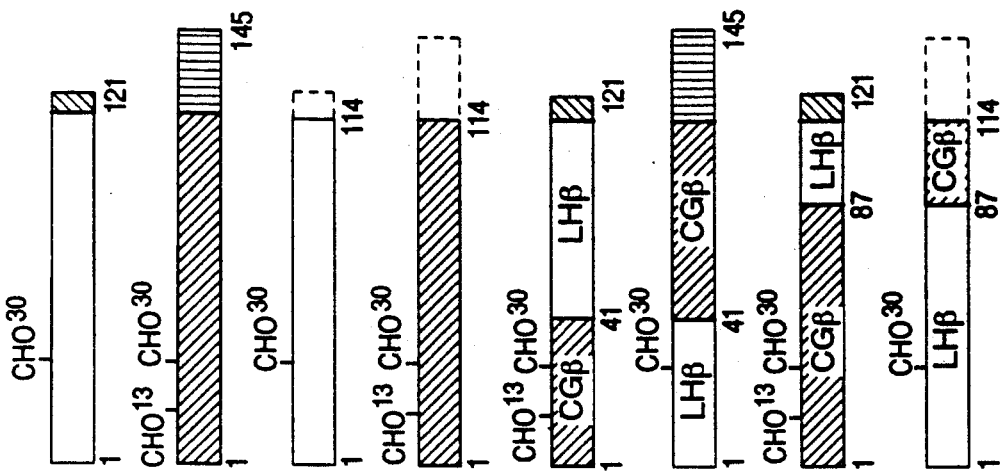
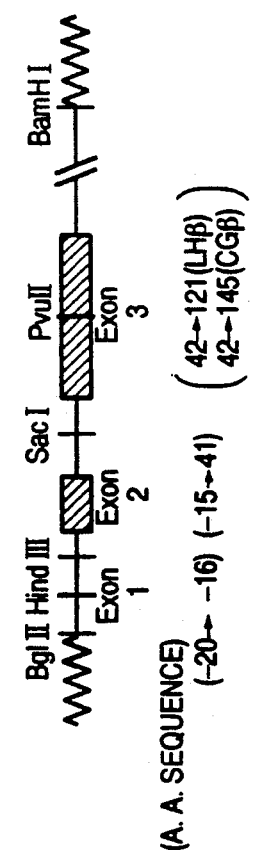
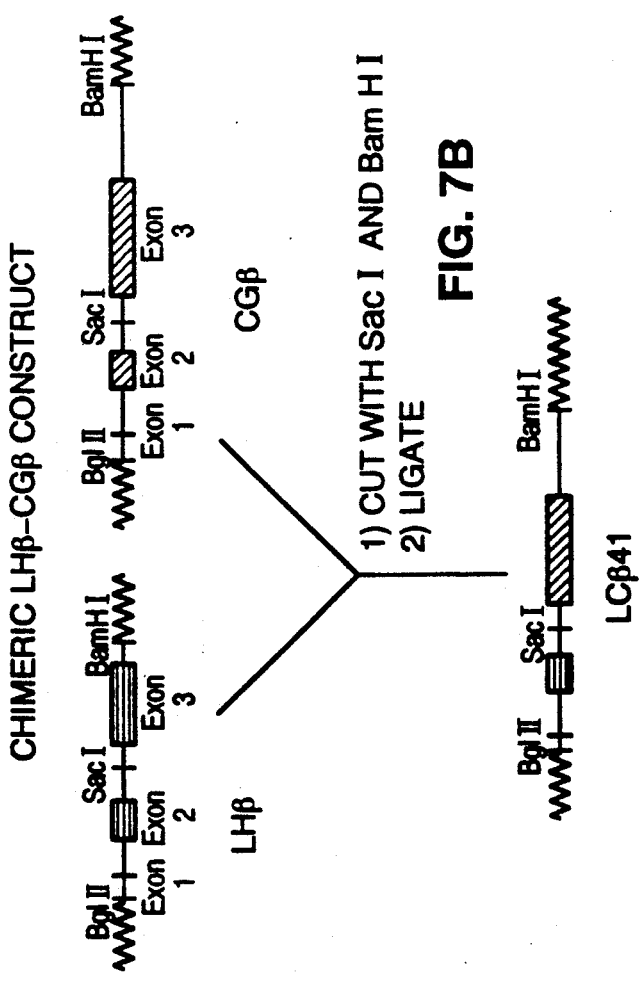
FIG. 7A
FIG. 7B
FIG. 7C

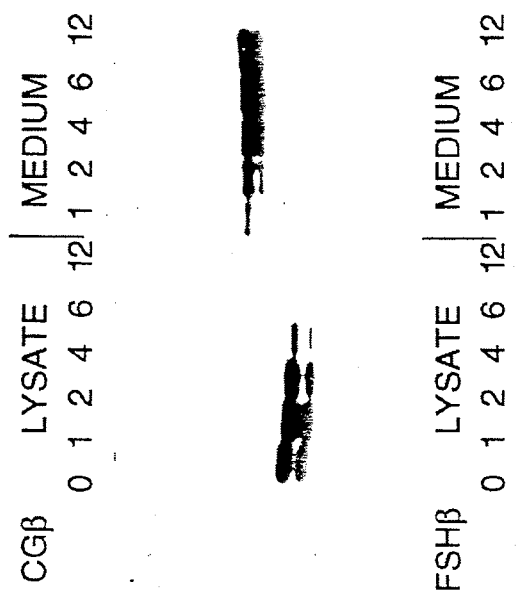
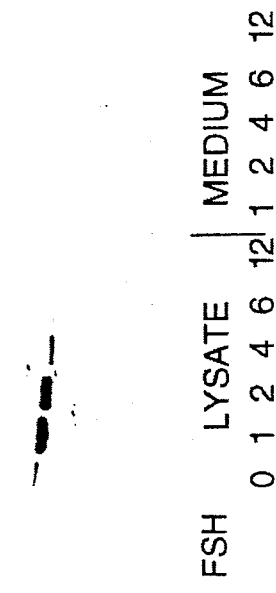
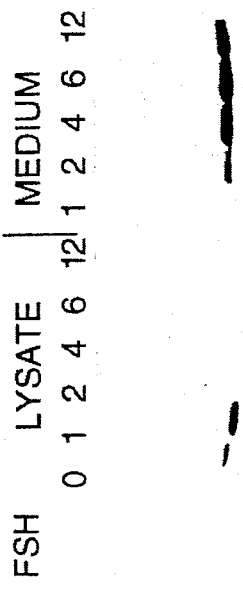
FIG. 9C  FIG. 9D  FIG. 9E
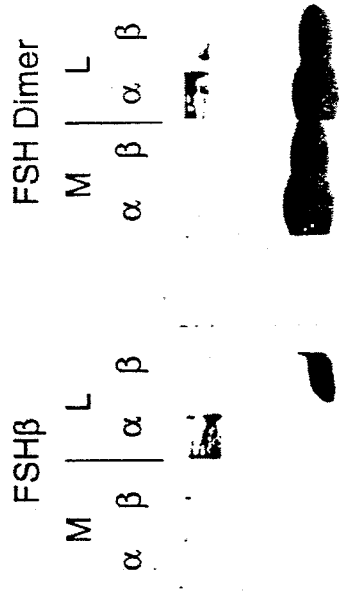
FIG. 9A  FIG. 9B

MODIFIED FORMS OF REPRODUCTIVE HORMONES

This invention was made with Government support under NIH Contract No. NO1-HD-9-2922 awarded by the National Institutes of Health. The Government has certain rights in the invention.

CROSS-REFERENCE TO RELATED PATENT

This is a continuation-in-part of U.S. Ser. No. 313,646 filed 21 Feb. 1989, and a continuation-in-part of the commonly owned PCT application, U.S. 90/01037, filed 20 Feb. 1990, both of which are herein incorporated by reference.

TECHNICAL FIELD

The invention relates to the production of human reproductive hormones with altered glycosylation patterns and activities, and to improved modified forms of the beta subunit of LH. In particular, it concerns production of recombinant hormones under conditions which result in efficient production and secretion and which regulate the glycosylation pattern of the protein, and to production of modified forms of LH with enhanced secretion and dimerization properties.

BACKGROUND ART

Human reproductive function is controlled in part by a family of heterodimeric human glycoprotein hormones which have a common alpha subunit, but differ in their hormone-specific beta subunits. The family includes follicle-stimulating hormone (FSH), luteinizing hormone (LH), thyrotropin or thyroid-stimulating hormone (TSH), and human chorionic gonadotropin (CG). In all cases, the alpha subunit is a 92 amino acid glycoprotein with two canonical glycosylation sites at the asparagines located at positions 52 and 78. The beta subunits are also glycoproteins; in addition to the N-linked glycosylation exhibited by the beta chains of all four hormones, human CG contains four mucin-like O-linked oligosaccharides attached to a carboxy-terminal extension unique to this hormone. The relevance of the O-linked glycosylation is not, apparently, related to the secretion and assembly of the hormone (Matzuk, M. M. et al. *Proc Natl Acad Sci U.S.A.* (1987) 84:6354-6358).

Genomic and cDNA clones have been prepared corresponding to the human alpha chain (Boothby, M. et al. *J. Biol Chem* (1981) 256:5121-5127; Fiddes, J. C. et al. *J Mol App Genet* (1981) 1:3-18). The cDNA and/or genomic sequences of the beta subunits have also been prepared. For CG, the beta-encoding DNA is described by Fiddes, J. C. et al. *Nature* (1980) 286:684-687 and by Policastro, P. et al. *J Biol Chem* (1983) 258:11492-11499. For luteinizing hormone, such description is by Boorstein, W. R. et al. *Nature* (1982) 300:419-422; and for TSH by Hayashizaki, Y. et al. *FEBS Lett* (1985) 188:394-400 and by Whitfield, G. K. et al. in "Frontiers in Thyroidology", (1986) Medeiros-Nato, G. et al. (eds) pages 173-176, Plenum Press, N.Y. These DNA segments have been expressed recombinantly, and biologically active material has been produced.

The genomic sequence encoding FSH beta chain was used to construct a recombinant expression vector containing the complete beta chain coding sequence as described in PCT application WO86/04589, published 14 Aug. 1986. In addition genomic clones for human FSH-beta have been prepared by others (Watkins, P. C. et al. *DNA* (1987) 6:205-212; Jameson, J. L. et al., *Mol Endocrinol* (1988) 2:806-815; Jameson, J. L. et al. *J Clin Endocrinol Metab* (1986) 64:319-327; Glaser, T. et al. *Nature* (1986) 321:882-887). However, it is not clear that human FSH beta has been engineered to permit recombinant production of the dimeric hormone. (The bovine beta FSH gene has also been obtained as disclosed in Maurer, R. A. et al. *DNA* (1986) 5:363-369; Kim, K. E. et al. *DNA* (1988) 7:227-333.)

The invention constructs permit significant recombinant production of this family of hormones, in particular, FSH and LH, and further sets forth a means for regulation of the glycosylation pattern and thereby greater predictability in the formulation of therapeutically useful materials.

While it is now understood that the glycosylation pattern of a particular protein may have considerable relevance to its biological activity, the importance of this pattern has largely been overlooked in characterization of glycoproteins. Emphasis has been placed on the amino acid sequence as if this were the sole component of the glycoprotein. The reasons for this myopia are largely historic, but this almost exclusive focus on the peptide aspect is clearly in error. For example, it is well known in the case of human CG that desialylation causes the hormone to be cleared rapidly via the liver (Morell, A. G. et al. *J Biol Chem* (1976) 246:1461-1467). It is also known that removal of carbohydrate internal to the sialic acid residues or complete deglycosylation converts human CG into an antagonist which binds more tightly to receptor but shows decreased biological activity in vitro (Channing, C. P. et al. *Endocrinol* (1978) 103:341-348; Kalyan, N. J. et al. *J Biol Chem* (1983) 258:67-74; Keutmann, H. T. et al. *Biochemistry* (1983) 3067-3072; Moyle, W. R. et al. *J Biol Chem* (1975) 250:9163-9169). Other glycoproteins, such as, for example, tissue plasminogen activator, are also known to be altered in their degree of activity when the glycosylation pattern is changed. Therefore, it appears that in order to regulate the therapeutic function of the glycoprotein hormones, it may be necessary to control both the level and nature of glycosylation.

Human FSH and LH are used therapeutically to regulate various aspects of metabolism pertinent to reproduction in the human female. For example, FSH partially purified from urine is used clinically to stimulate follicular maturation in anovulatory women with anovulatory syndrome or luteal phase deficiency. Luteinizing hormone (LH) and FSH are used in combination to stimulate the development of ovarian follicles for in vitro fertilization. The role of FSH in the reproductive cycle is sufficiently well-known to permit this sort of therapeutic use, but difficulties have been encountered due, in part, to the heterogeneity and impurity of the preparation from native sources. This heterogeneity is due to variations in glycosylation pattern. Similarly, LH is used therapeutically to alleviate conditions associated with impaired functioning of the female reproductive system.

DISCLOSURE OF THE INVENTION

The invention provides recombinantly produced human heterodimeric hormone of the group FSH, LH, TSH and CG, by improved means and by means which offer the opportunity for control of glycosylation pattern both on the alpha and beta portions of the heterodimer. Such glycosylation control can be obtained through either the prudent selection of the recombinant eucaryotic host, including mutant eucaryotic hosts, or through alteration of glycosylation sites through, for example, site directed mutagenesis at the appropriate amino acid residues. In any event, the recombinant production of these hormones obviates the complex mixture of glycosylation patterns obtained when the hormone is isolated from native sources.

The pM2/alpha vector disclosed herein containing the minigene is particularly efficient in providing for expression of the dimeric hormones of this family. The minigene could, of course, be ligated into a variety of host vectors and placed under the control of suitable promoters compatible with a eucaryotic host. Similarly, the beta subunit may also be provided with alternate control systems. Efficient production of these hormones using the alpha minigene is one aspect of the invention.

In another aspect, the invention is directed to specific mutants of this family with altered glycosylation patterns at the two glycosylation sites in the alpha subunit, or to alpha subunit variants containing alterations at the carboxy terminus which affect activity. Thus, in this aspect, the invention is directed to expression systems for muteins of the alpha subunit which lack glycosylation sites at the asparagine at position 52 or position 78 or both, or contain modifications at positions 88-92, and to recombinant host cells transfected with these expression systems. The modifications at positions 88-92 are especially important as they result in a diminution or elimination of the steroidogenetic activity of the hormones, but do not effect receptor binding. Therefore, analogs to the hormones produced using these modifications can be used as antagonists. The cells may be transfected with this subunit expression system singly or in combination with an expression system for a suitable beta subunit. The invention is directed also to the mutant glycoproteins with altered glycosylation or activity patterns produced by these cells.

In another aspect, the invention is directed to modified forms of LH beta chain wherein the 7-amino acid hydrophobic sequence at positions 115-121 is deleted or replaced by a hydrophilic sequence, and at least one residue selected from the group consisting of trp[8], ile[15], and met[42] is replaced by a hydrophilic amino acid, or thr[58] is replaced by asn. In preferred embodiments, the hydrophilic amino acid most like the hydrophobic residue replaced is used as the substitute, or the amino acid, in the corresponding position in the CG beta claim is substituted. Also preferred are embodiments wherein the hydrophobic sequence at positions 115-121 is replaced by the carboxy terminal peptide of human CG beta subunit or a variant thereof as described below. Also included within the invention are DNA sequences encoding this modified LH beta and recombinant materials and methods for the production of this subunit, either alone or in the presence of alpha subunit.

In still another aspect, the invention is directed to the recombinant production of FSH wherein the resulting dimer contains an extended form of the FSH beta chain i.e. the FSH beta sequence fused to the carboxy terminal portion (CTP) of the CG sequence or a variant thereof. This modified form of FSH is very efficiently produced and secreted.

The carboxy terminal portion of the CG beta subunit or a variant of this carboxy terminal peptide has significant effects on the clearance of CG, FSH, and LH. This extension at the carboxy terminus has similar effects on the clearance of hormones and of protein-based pharmaceuticals in general. Therefore, another aspect of the invention is directed to modified forms of peptide or protein pharmaceuticals wherein the modification comprises ligation of the CTP or its variant to the carboxy terminus of said protein or peptide. Especially preferred proteins or peptides are the peptide hormones.

In other aspects, the invention is directed to pharmaceutical compositions containing the variants set forth above, and to methods to regulate reproductive metabolism in subjects by administration of these glycoproteins or their pharmaceutical compositions.

BRIEF DESCRIPTION OF THE DRAWINGS

FIG. 2 shows the nucleotide sequence of the human FSH beta gene.

FIG. 3A shows the construction of the human alpha subunit minigene, and 3B shows the construction of expression vectors comprised of the alpha subunit minigene.

FIG. 6 shows a comparison of the amino acid sequences of human CG and human LH beta subunits.

FIGS. 7A-C show the construction of various LH chimeras and muteins.

FIGS. 9A-E show autoradiographs of SDS-PAGE gels displaying 35-S cysteine labeled FSH or FSH beta immunoprecipitated from cell lysates and media.

MODES OF CARRYING OUT THE INVENTION

Definitions

Figure 1:
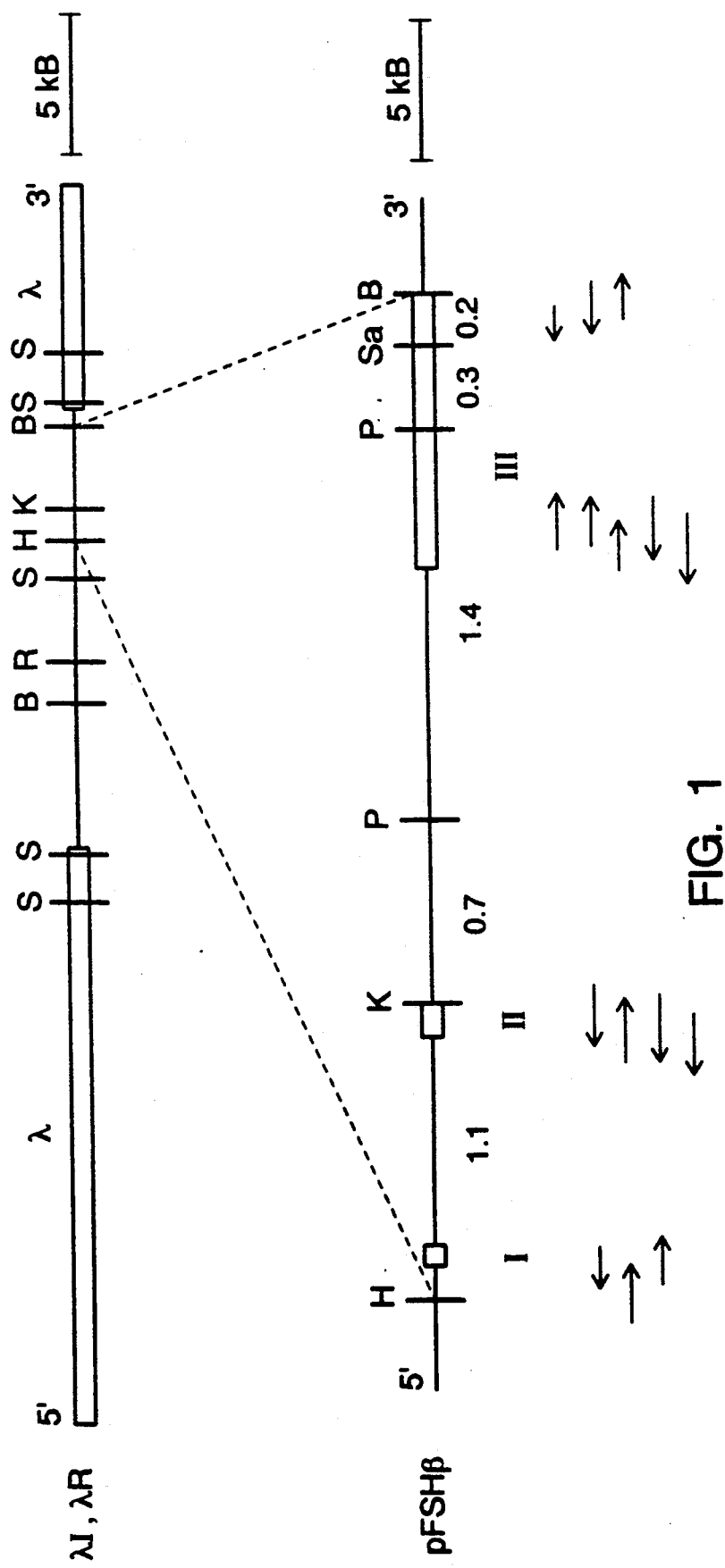
FIG. 1 shows a restriction enzyme map of the human FSH beta gene.

As used herein, human alpha subunit, and human FSH, LH, TSH, and CG beta subunits as well as the heterodimeric forms have in general their conventional definitions and refer to the proteins having the amino acid sequences known in the art per se, or allelic variants thereof, deliberately constructed muteins thereof maintaining the activity of the native protein regardless of the glycosylation pattern exhibited, or mutant forms thereof having at least 90% homology with the native forms.

"Native" forms of these peptides are those which have the amino acid sequences isolated from human tissue, and have these known sequences per se, or their allelic variants.

"Mutein" forms of these proteins are those which have deliberate alterations in amino acid sequence produced by, for example, site-specific mutagenesis or by other recombinant manipulations, or which are prepared synthetically. These alterations result in amino acid sequences wherein the biological activity of the subunit is retained and/or wherein the subunit has at least 90% homology with the native form.

A preferred mutein of the alpha subunit for use in antagonists of the various heterodimers has alterations in the amino acids of positions 88-92.

A particularly preferred mutein of FSH beta, for example, is an "extended" FSH beta wherein the amino acid sequence comprising the carboxy terminal peptide (CTP) of hCG is fused to the carboxy terminus of FSH beta. As used herein, "CTP" refers to the "extra" sequence at the C-terminus of the CG beta peptide as compared to the other related hormones. The length of the effective CTP as compared to the other beta subunits may vary slightly but it extends from roughly amino acid 112-118 of CG to residue 145 at the C-terminus. The precise length of CTP in the constructs herein will be clear from the content.

In the fusions described herein, native CTP can be used or a "variant" thereof. By "variant" is meant a conservative analog of the peptide residues from about 112-118 to 145, i.e. this sequence wherein about 1-5 amino acids of the sequence are altered without substantial change in properties. Often this variation results simply from mutation to obtain appropriate restriction sites.

Although it is recognized that glycosylation pattern has a profound influence on activity both qualitatively and quantitatively, for convenience the terms FSH, LH, TSH, and CG beta subunits refers to the amino acid sequence characteristic of the peptides, as does "alpha subunit". When only the beta chain is referred to, the terms will be, for example, FSH beta; when the heterodimer is referred to, the simple term "FSH" will be used. It will be clear from the context in what manner the glycosylation pattern is affected by, for example, recombinant expression host or alteration in the glycosylation sites. Forms of the glycoprotein with specified glycosylation patterns will be so noted.

As used herein, the alpha subunit "minigene" refers to the gene construction disclosed herein in the description of the construction of pM²/CG alpha or pM²/alpha (See FIG. 3B). This "minigene" is characterized by retention only of the intron sequence between exon III and exon IV, all upstream introns having been deleted. In the particular construction described, the N-terminal coding sequences which are derived from exon II and a portion of exon III are supplied from cDNA and are ligated directly through an XbaI restriction site into the coding sequence of exon III so that the introns between exons I and II and between exons II and III are absent. However, the intron between exons III and IV as well as the signals 3' of the coding sequence are retained. The resulting minigene can conveniently be inserted as a BamHI/BglII segment. Other means for construction of a comparable minigene are, of course, possible and the definition is not restricted to the particular construction wherein the coding sequences are ligated through an XbaI site. However, this is a convenient means for the construction of the gene, and there is no particular advantage to other approaches, such as synthetic or partially synthetic preparation of the gene. The definition includes those coding sequences for the alpha subunit which retain the intron between exons III and IV but no other introns.

A "transfected" recombinant host cell, i.e., a cell "transfected" with the recombinant expression systems of the invention, refers to a host cell which has been altered to contain this expression system by any convenient manner of introducing it, including transfection, viral infection, and so forth. "Transfected" refers to cells containing this expression system whether the system is integrated into the chromosome or is extrachromosomal. The "transfected" cells may either be stable with respect to inclusion of the expression system or not. In short, recombinant host cells "transfected" with the expression system of the invention refers to cells which include this expression system as a result of their being manipulated to include it, when they in their native state do not, regardless of the manner of effecting this incorporation.

"Expression system" refers to a DNA sequence which includes a coding sequence to be expressed and those accompanying control DNA sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

As used herein "cells", "cell cultures", and "cell lines" are used interchangeably without particular attention to nuances of meaning. Where the distinction between them is important, it will be clear from the context. Where any can be meant, all are intended to be included.

ISOLATION OF THE GENE ENCODING FSH BETA

An important aspect of the present invention is the provision of an expression system for FSH beta-encoding DNA which provides beta-FSH that readily dimerizes to form the hormone. The gene, suitable for inclusion in expression systems intended for host cells capable of processing introns, was prepared as follows:

Genomic DNA from JAr choriocarcinoma cells (a human placental donor) was partially digested with MboI and cloned into the BamHI site of lambda MG3, a vector described Helms, C., et al. *DNA* (1985) 4:39-49; this vector is a derivative of lambda L47 which is described by Loenen, W. A. M., et al. *Gene* (1980) 10:249-259. The size of the inserts was typically 15-20 kb. Approximately $5 \times 10^5$ plaques were obtained and screened according to the method of Benton, W. D., et al. *Science* (1977) 196:180-182 using the 41 mer encoding amino acids 94-107 of exon III of human FSH beta as described by Watkins, P. C., et al. *DNA* (1987) 6:205-212. This 41 mer has the sequence:

TGTACTGTGCGAGGCCTGGGGCCCAGC-
TACTGCTCCTTTGG.

Two positive clones were isolated by repeated plaque purification and shown by restriction analysis to be identical; furthermore, the PstI cleavage patterns were consistent with those obtained by Glaser, T. et al. *Nature* (1986) 321:882-887 (supra). Restriction fragments were subcloned into pUC18 for further restriction analysis and into M13 for sequencing by the dideoxy chain termination method of Sanger, F., *Proc Natl Acad Sci U.S.A.* (1977) 74:5463–5467. A 3.7 kb HindIII/BamHI fragment contained in the 16.5 kb insert of these clones contains the hFSH beta coding sequence.

The clones were designated lambdaI and lambdaR, and have identical restriction maps and are approximately 16.5 kb in length. The restriction map of the full length clones are shown in FIG. 1, along with a restriction map of the 3.7 kb human FSH beta coding sequence.

The results of sequencing the human FSH beta gene are shown in FIG. 2. As shown in FIG. 2, the coding sequence is divided into three exons. Exon I contains a 5' untranslated tract previously reported to encode two transcripts of either 33 or 63 bp (Jameson, J. L. et al. *Mol Endocrinol* (1988) 2:806–815). Exon II encodes an 18 amino acid signal peptide and amino acids 1–35 of the mature protein. Exon III encodes amino acids 36–111 and about 1.1 kb of 3' untranslated sequence. Exons I and II are separated by an intron of about 800 bp, and exons II and III by an intron of about 1.4 kb.

The nucleotide sequence obtained is similar to that reported by Watkins, T. C. et al. *DNA* (1987) 6:205–212 and Jameson, J. L. et al. (supra), except that tyrosine 58 is encoded by TAC rather than TAT and there are differences from Watkins in the 3' and 5' untranslated regions. A putative transcriptional start site 32 bp downstream from the TATA element is assigned by analogy to the bovine gene reported by Kim, K. E., et al., *DNA* (1988) 7:227–333. The sequence in FIG. 2 shows a single polyadenylation signal (AATAAA) overlapping the termination codon and recent evidence from the bovine gene (supra) and human clones (Jameson, J. L. et al., (supra)) indicates the presence of an approximately 1.1 kb 3' untranslated tract which may contain alternate polyadenylation signals.

The amino acid sequence shown in FIG. 2 is identical to that reported by that of Watkins (supra) but differs from that reported earlier by protein sequencing of purified human FSH beta. The carboxy terminal sequence Tyr-Pro-Thr-Ala-Leu-Ser-Tyr reported by Saxena, D. B., *J Biol Chem* (1976) 251:993–1005 is found neither in the sequence shown in FIG. 2 nor in the protein based sequence reported by Shome, B., et al., *J Clin Endocrinol Metab* (1974) 39:203–205. A more recent determination of the amino acid sequence confirms the sequence deduced from the DNA (Stone, B. et al. *J Prot Chem* (1988) 7:325–339.

An important modification of the beta-FSH chain encoding DNA is obtained when the 34 amino acid carboxy terminal peptide (CTP) of the chorionic gonadotropin beta chain is fused to the C-terminus. In this form of the hormone, the C-terminal Glu of FSH beta at position 111 is extended with the amino acid sequence representing from about amino acids 112–118 to 145 of the beta CG sequence.

CONSTRUCTION OF EXPRESSION VECTORS FOR NATIVE HUMAN ALPHA SUBUNIT AND ITS MUTEINS

The alpha subunit used in the constructions of the invention is advantageously in the form of the minigene as described above. It has been found that the use of the minigene enhances the production of the alpha subunit as well as its capacity to dimerize with the appropriate beta subunit to form the desired heterodimer. The minigene or the other forms of DNA encoding the alpha subunit can also be modified to provide alpha subunit muteins. Some of these are particularly useful as antagonists, such as those having deletions or alterations in amino acids at positions 88–92 of the native sequence. In addition, the gene encoding the alpha subunit can be modified so as to provide glycosylation mutants.

It is understood in the art that N-linked glycosylation occurs at the tripeptide site Asn-X-Thr/Ser, two of which sites occur in the human alpha subunit, at Asn52 and Asn78. Site-directed mutagenesis was performed on a human alpha subunit fusion gene to alter these sites, wherein the fusion gene was constructed as follows:

The alpha subunit cDNA is obtained as described by Matzuk, M. M. et al. *J Cell Biol* (1988) 106:1049–1058, incorporated herein by reference (supra) as a BamHI/XhoI framed nucleotide sequence containing an XbaI site in the coding sequence (FIG. 3A)). A genomic fragment bounded by EcoRI and a XhoI site containing exons III and IV, with an XbaI site in exon III was obtained from the human choriocarcinoma library (FIG. 3A). XbaI/XhoI digestion of both the genomic fragment and alpha subunit cDNA, followed by religation at the XbaI site creates the alpha subunit minigene as a BamHI/XhoI fragment, containing a BglII site derived from the genomic fragment downstream of exon IV. The reconstructed gene contains two coding regions (exon II and III and exon IV), a single intron, and the polyadenylation signals 3' to exon IV. The BamHI/BglII fragment digested from the minigene is used as the alpha subunit-encoding insert in the construction of expression vectors (FIG. 3B). The use of the alpha subunit minigene gives impressive and surprising results in affecting the efficiency of expression systems for production of the dimeric hormones.

In constructing genes encoding muteins of the alpha subunit, the BamHI/XhoI fragment itself is ligated into M13 UM20 for site-directed mutagenesis. For alteration of Asn52 and Asn78, respectively, the 22-mer oligomers GGTGACGTCCTTTTGCACCAAC and CTTAGTGGAGCGGGATATG respectively were used. This resulted in a substitution of aspartate residues for asparagine. Three mutants were constructed: alpha(Asn1) (position 52), alpha(Asn2) (position 78), and alpha(Asn1+2) (both positions). Corresponding changes were made by substituting the codon for alanine in place of that for threonine at positions 54 and 80 using the 26 mers: GTGGACTCTGAGGCCACGTTCTTTTG and CAGTGGCACGCCGCATGGTTCTCCAC, respectively to obtain alpha(Thr1), alpha(Thr2) and alpha(Thr1+2).

The wild type or mutant alpha subunits were then ligated into the host vector pM² as the 2.4 kb minigenes as BamHI/BglII segments so as to be placed under control of the LTR promoter by insertion into the BamHI site downstream of the LTR, as shown in FIG. 3B. pM², as described by Matzuk, M. M. et al., *Proc Natl Acad Sci U.S.A.* (1987) 84:6354–6358, is a derivative of pSV2Neo and contains the ampicillin resistance gene (amp$^r$), the neomycin resistance gene (neo$^r$), and the Harvey murine sarcoma virus long terminal repeat (LTR) promoter with a unique downstream BamHI site. pM²/alpha contains an alpha subunit minigene downstream from a second LTR. The resulting vector shown, pM²/CG alpha, can be used to express the alpha subunit per se or can be used as the source of the human alpha expression unit for construction of a host vector which can also accommodate the expression of an additional DNA. One example of useful additional DNA comprises those encoding the various beta hormone chains.

The host vector pM2/alpha may be prepared by excising this alpha expression unit from pM2/CG alpha as an EcoRI/EcoRI fragment and ligating it into the EcoRI site of pM2 (Matzuk, M. M. et al. *Mol Endocrinol* (1988) 2:95-100) incorporated herein by reference and also shown in FIG. 3B. As therein described, the BamHI site at the 5' end of the gene is first deleted, and the XhoI site at the 3' end of the gene is converted to an EcoRI site using oligonucleotide linkers. This vector can then also accommodate a DNA encoding a beta subunit.

In addition to muteins of the alpha subunit which have altered glycosylation patterns, a group of muteins with reduced or zero activity in signal transduction is also prepared. Experiments using chemical derivatization in in vitro assays indicate that amino acids at positions 88-92 (tyr-tyr-his-lys-ser) are necessary for the signal transduction activity of the hormone. Accordingly, deletion or alteration of one or more of these amino acids by site-directed mutagenesis results in analogs which continue to bind to receptor but have reduced or negligible activity. All four of the hormones sharing this alpha subunit can thus be prepared as antagonists for the relevant hormone.

Both the wild type and mutant vectors can be used as a source of human alpha subunit, and provide host expression systems for recombinant production of the dimeric hormones. Of particular importance are mutants of the alpha subunit in which the glycosylation site at Asn-52 is altered. Such mutated sequences when ligated into expression systems and transfected into appropriate host cells result in production of proteins which, when combined with the appropriate beta subunit have antagonist activity for the relevant hormone.

The foregoing constructions are, of course, merely illustrative of expression vectors or systems which can be constructed for the production of alpha subunits or the corresponding heterodimeric hormones. Alternate control sequences including, for example, different promoters, can be ligated to the coding sequence of human beta subunits or the alpha minigene to effect expression in other eucaryotic cells which will provide suitable glycosylation. A variety of control sequences is known in the art, and methods to ligate the beta subunits or alpha minigene coding sequence are of course also available. For example, suitable yeast promoters include promoters for synthesis of glycolytic enzymes including those for 3-phosphoglycerate kinase, or promoters from the enolase gene or the leu2 gene. Suitable mammalian promoters include the early and late promoters from SV40, or other viral promoters such as those derived from polyoma, adenovirus 2, bovine papilloma virus or avian sarcoma viruses. Suitable viral and mammalian enhancers can also be used. Expression in insect cells using a baculovirus promoter has also been reported. While less common, expression systems suitable for plant cells are also available.

CONSTRUCTION OF VECTORS FOR THE BETA SUBUNITS

With respect to the coding DNA for beta subunits, such as FSH-beta or LH-beta, or their modified forms, genomic DNA or modified genomic DNA can be inserted directly into expression systems intended for eucaryotic host cells capable of processing introns. The nucleic acid sequences encoding the protein can be used directly from the genomic clone or cDNA clone as described herein, or can be entirely or partially synthesized using standard solid phase oligonucleotide synthesis techniques as described, for example, by Nambiar, K. P. et al. *Science* (1984) 223:1299 or by Jaye, E. et al. *J Biol Chem* (1984) 259:6311. These techniques are now commercially available. It is evident, of course, that not only the specific native nucleotide sequences can be employed, but also nucleotide sequences employing codons which are degenerate with these, as well as allelic forms.

CONSTRUCTION OF EXPRESSION VECTORS FOR FSH

To obtain satisfactory expression of FSH, one useful expression construct results from insertion of the beta subunit into a host vector in a position so as to be under control of an appropriate promoter wherein the host vector includes an expression system for the alpha minigene, such as pM2/alpha. When inserted as the HindIII/BamHI fragment, the FSH will be operably linked to the LTR promoter of its expression system. In an illustrative construction, the 5' HindIII site of FSH beta-containing pUC18 vector (pFSH beta), was converted to a BglII site using oligonucleotide linkers, and the modified pFSH beta vector digested with BglII and BamHI. The resulting 3.7 kb BglII/BamHI fragment was inserted into the unique BamHI site downstream of the LTR promoter which lacks a tissue-specific element so as to be operably linked to said promoter, and orientation was confirmed by restriction analysis.

Figure 4A:
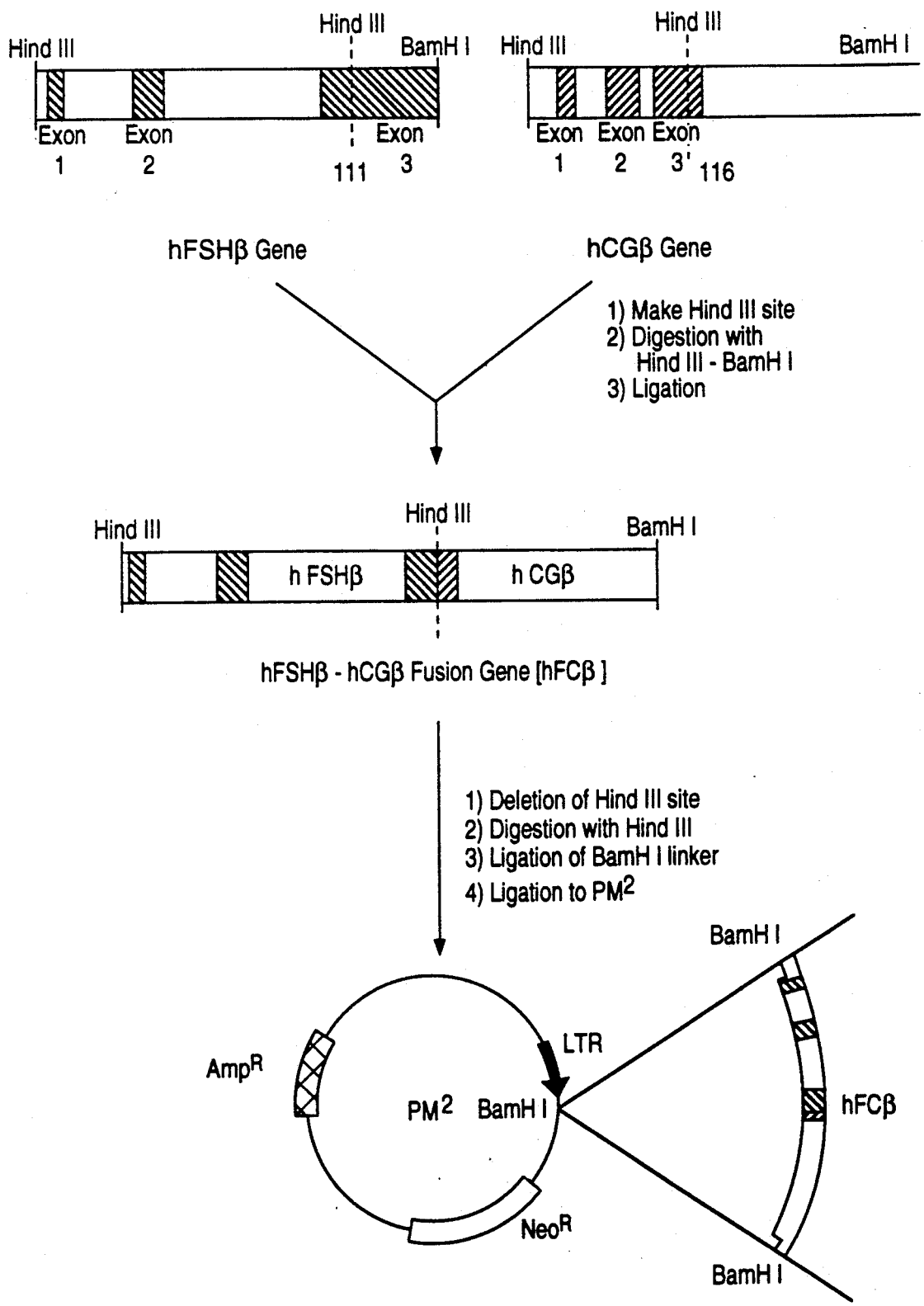
FIG. 4A shows the construction of the gene encoding the extended form of the FSH beta subunit, and the construction of an expression vector comprised of that gene; 4B shows the DNA sequence modifications required for the construction of the gene.
Figure 4B:
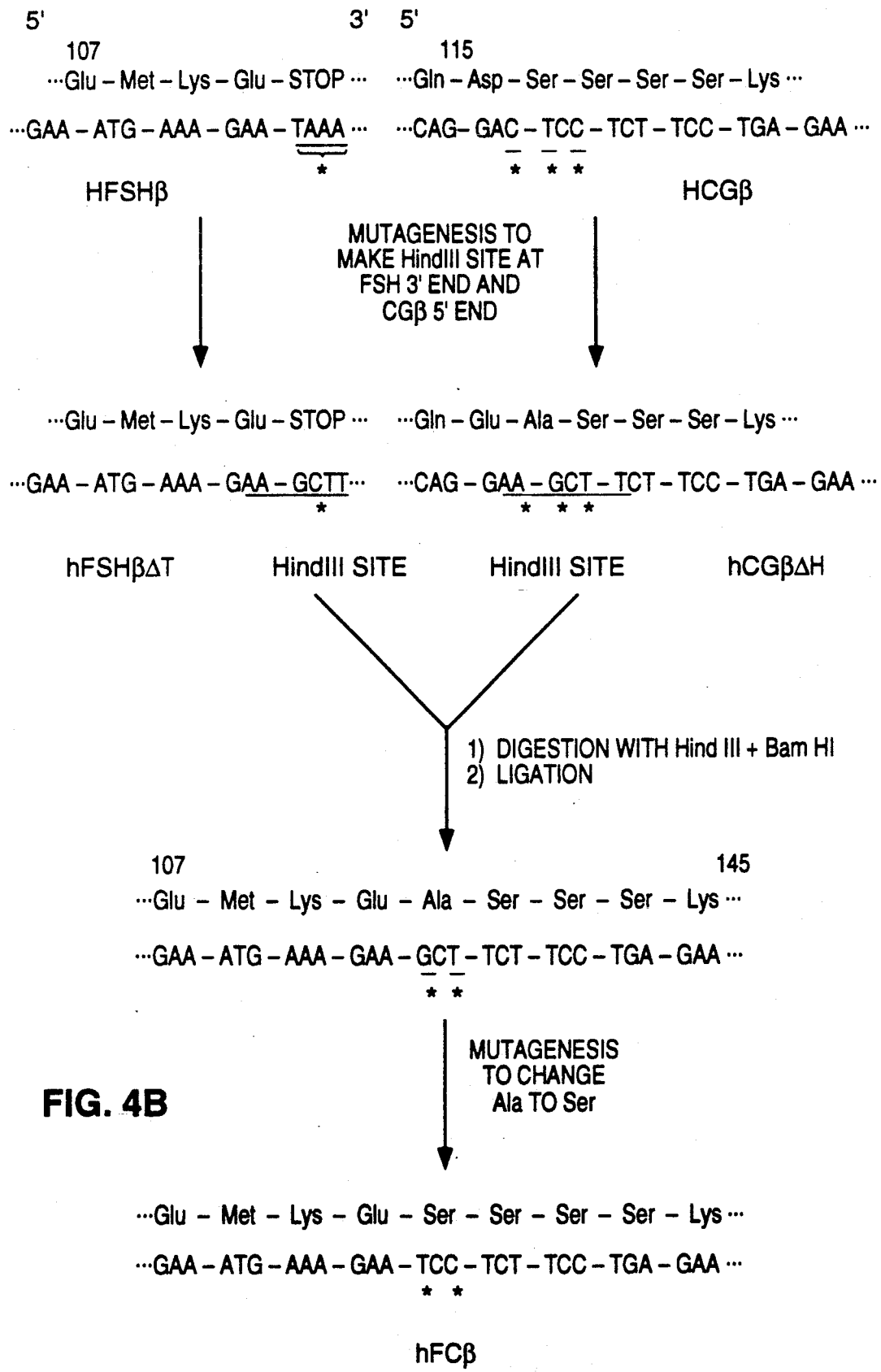

An important mutein-encoding sequence of FSH beta is obtained by ligating the DNA sequence encoding the carboxy terminal extension peptide of CG beta (CTP) to the 3' end of the FSH beta encoding sequence. To the C-terminal Glu of FSH beta at position 111 is ligated the downstream sequence of from about amino acid 112 to 118 to the carboxy terminal amino acid 145 of CG beta, or a variant thereof (FIG. 4A). Preferred variants include those wherein the Ser at position 118 of CG beta is replaced by Ala as shown in FIG. 4B. This extended form is conveniently obtained by ligation of HindIII-digested FSH beta encoding insert with the HindIII digest of CG beta cDNA, where this religation results in the Ser→Ala substitution.

Figure 5:
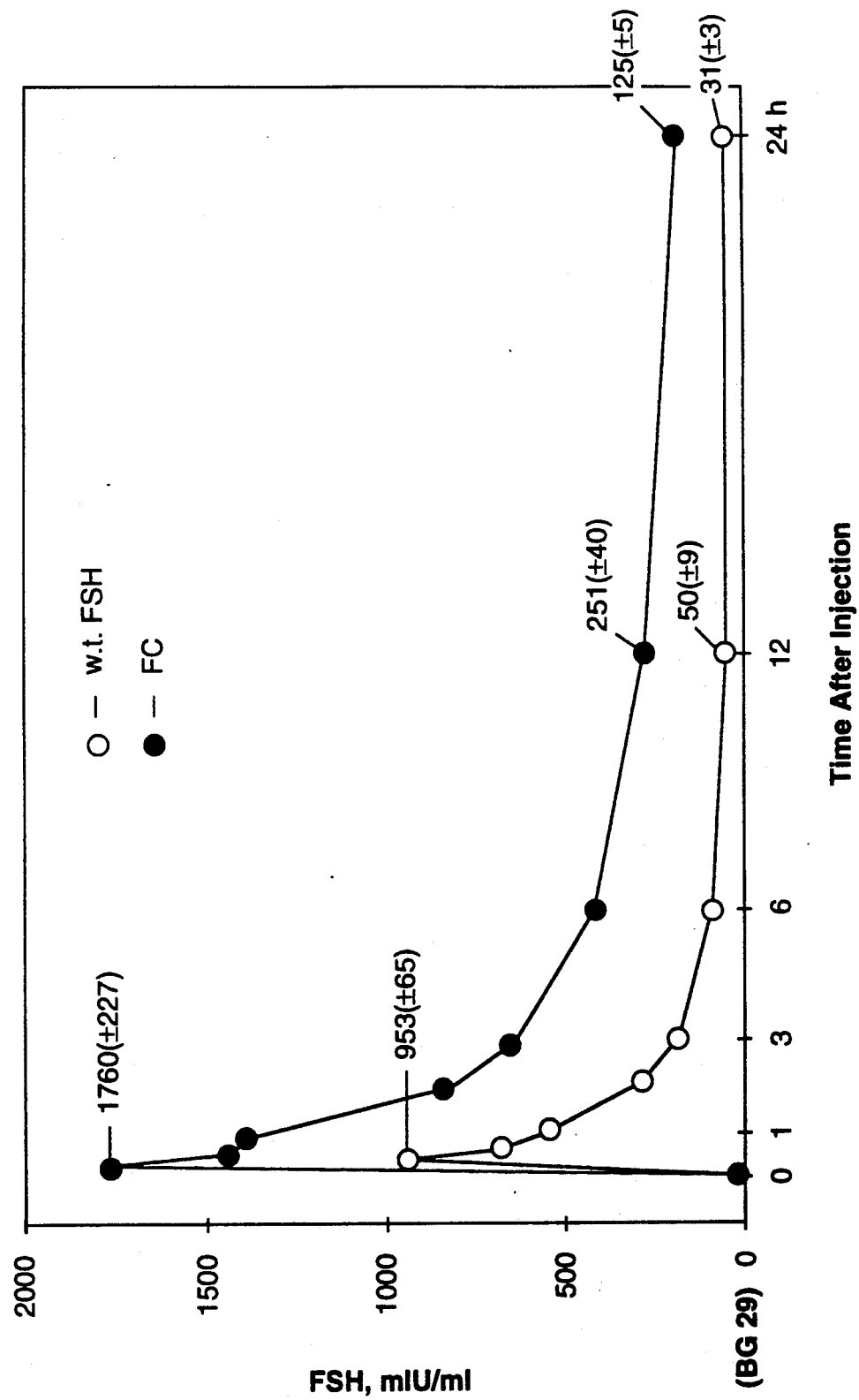
FIG. 5 demonstrates the effect of CTP on the half life of FSH analogs in the circulation.

The protein resulting from expression of this sequence when produced as a heterodimer FSH, i.e. .—FC, had the biological activity of native FSH but a prolonged circulating half-life as shown in FIG. 5. In this experiment rats were injected with either FC or the wild type FSH. Blood was collected at the times indicated and the hormone presented was measured by radioimmunoassay. This result was anticipated in view of the longer half-life of CG as compared to LH, which is ascribable to the presence of extensive O-linked glycosylation in the CTP region as described by Van Hall, E. *Endocrinol* (1971) 88:456. A major problem with FSH in clinical use is the relatively short circulating half-life of this protein (Wide, L. *Acta Endocrinol* (1986) 112:336).

Thus, "extended" forms of FSH beta are those wherein the approximately 28-34 amino acid sequence represented by residues 112-118 to 145 of human CG (or a variant thereof) is ligated to the C-terminus of FSH-beta. As stated above, "variant" is meant a conservative analog of the peptide residues from about 112-118 to 145, i.e. this sequence wherein about 1-5 amino acids of the sequence are altered without substantial change in properties.

The construction of one embodiment of this extended form of FSH is outlined in FIG. 4B. As shown, the coding sequence for human FSH beta for the C-terminal portion located in the third exon of the human FSH beta gene is mutated in the stop codon to obtain a HindIII site. Similarly, the region encoding the beginning of the CTP region of the human CG beta subunit, also in the third exon of the gene, is mutated at positions 116 and 117 to obtain a corresponding HindIII site. This mutation converts the Asp residue at position 116 to glutamic and the serine residue at position 117 to Ala. The mutated genomic fragments are then digested with HindIII and BamHI and ligated as shown to obtain a fragment encoding the extended FSH beta; if desired further mutagenesis is performed to convert the Ala residue to a hydrophilic Ser residue. The FSH beta subunit, thus contains the region of beta CG at positions 118-145. The BamHI/BamHI fragment containing the modified beta FSH encoding sequence is then ligated into the BamHI site of pM$^2$ under control of the LTR promoter.

When cotransformed into Chinese hamster ovary cells along with the expression vector for the alpha subunit pM$^2$/alpha, yields of secreted FC of approximately 1 mg/$10^6$ cells/24 hr cultured in 1 L of medium were obtained. It was found that the extended FSH$\beta$ subunit quantitatively associated with the $\alpha$ subunit to form the FC heterodimer. FC was rapidly and quantitatively secreted as a dimer, and its bioactivity in vitro is comparable to the wild type FSH hormone activity.

Additional muteins of FSH beta are prepared by deleting or altering the N-linked glycosylation sites represented by the Asn-Thr combinations at positions 7/9 and 24/26 of the native sequence. The protein produced from expression of a system capable of expressing the genes encoding these muteins is expected to show adequate receptor binding with respect to the FSH beta receptor, and when heterodimerized with a suitable alpha subunit can be used as an antagonist for FSH activity; or, when heterodimerized with a normal alpha subunit can be used as an FSH substitute.

CONSTRUCTION OF EXPRESSION VECTORS FOR HUMAN LH MUTEINS

Difficulties have been encountered in the art in the production of LH using recombinant techniques because the LH beta chain, for example, compared to the chorionic gonadotropin (CG) beta chain, fails to dimerize efficiently to the alpha subunit and is not secreted when obtained as the monomer. The mutein LH beta chains of the invention do not suffer from these disadvantages.

The effect of various alterations of the LH encoding sequence on secretion of the LH chain alone or on dimerization and secretion of the intact hormone can be determined by expressing the LH-encoding sequence in cells transformed with a suitable vector containing an expression system encoding LH beta alone or in cells which coexpress the alpha subunit. In the latter case, the alpha subunit expression system can either be supplied on a separate vector, such as pM$^2$/CG alpha, or can be supplied on a vector which also contains the beta subunit. This can be done, for example, by insertion of the gene encoding the beta subunit into the host vector pM$^2$/alpha described above.

FIG. 6 shows the differences in amino acid sequence between the beta chains of LH and CG in humans. A reading frame shift after the codon for position 114 in LH as compared to CG leads to the translation of a hydrophobic 7 amino acid sequence which forms the C-terminus of LH contrasted with the relatively hydrophilic 31 amino acid sequence which provides the C-terminal peptide (CTP) of CG in this case, residues 115-145. In the muteins of the invention, the 7 amino acid hydrophobic C-terminus of LH is deleted or replaced with a hydrophobic sequence. In addition, one or more substitutions are made for the amino acids which inhibit secretion or dimerization. These LH amino acids are selected from the group consisting of the tryptophan residue at position 8 (trp$^8$), the isoleucine residue at position 15 (ile$^{15}$), the methionine residue at position 42 (met$^{42}$) and the aspartic acid residue at 77 (asp$^{77}$). The combination of these modifications results in beta LH subunits which are easily secreted. In addition, the combination of the deletion or replacement of the 7 carboxy terminal amino acid sequence in combination with at least one substitution for an amino acid selected from the group consisting of trp$^8$, ile$^{15}$, met$^{42}$ and the threonine at position 58 (thr$^{58}$) enhances dimer formation when the alpha subunit is coexpressed. Other substitutions may also be made, but the combination of the alteration or deletion of the 7 amino acid terminus with the alteration of one of the above-specified amino acids is necessary to have the desired effect.

The construction of genes encoding these modified forms of LH will permit the construction of cell lines to produce the desired hormone analog for the provision of quantities of the analog useful for therapeutic and/or diagnostic purposes.

As stated in the Background section, the DNA sequence encoding the beta LH chain is readily available. In the illustration below, the wild type LH-encoding starting material was provided as a 1270 bp HindIII/BamHI fragment containing the coding sequences of exons II and III of the LH beta gene.

As further described below, in two preferred embodiments, the 7 amino acid sequence at the C-terminus of LH can either be deleted directly by insertion of a stop codon after the codon for amino acid 114, or can be replaced by a hydrophilic sequence, preferably the CTP from human CG, or a variant thereof. The replacements for the additional interfering amino acids at the above-referenced positions are those which destroy the anti-secretion or anti-dimerization effects of these amino acids. Table 1 shows illustrative modified forms of the beta subunit which were prepared by mutagenesis after insertion of the LH beta gene into M13mp19 and hybridization with the appropriate oligonucleotides. After the mutagenesis, the modified HindIII/BamHI fragment was ligated to the sequence of exon I to provide the LH beta fragment as a 1400 bp BglII/BamHI fragment. However, in variants where the gene contained the CTP region of the CG sequence, the BglII/BamHI fragment contained 3600 bp.

The construction of the genes encoding the various LH muteins and LH/CG chimeras is outlined in FIG. 7. Expression systems for both chimeras of LH and CG beta subunits and muteins were engineered and tested for the ability to produce subunits which are readily secreted and/or from dimers. As shown in FIG. 6, the chimeras are constructed by using the appropriate portions of the LH beta or CG beta encoding genes. The chimeras are noted by LC or CL, depending on which of the subunits forms the N-terminus and which the C-terminus, and the number following the designation designates the number of the last amino acid in the beta subunit which forms the N-terminus. Thus, LCbeta41 shown in FIG. 7 produces a beta subunit which contains amino acids 1–41 of human LH beta subunit as its N-terminus and amino acids 42–145 of human CG beta subunit at its C-terminus. As the beta subunit is understood, it is deleted from the designation in the text. CL87 designates a construct which contains amino acids 1–87 of CG followed by amino acids 88–121 of LH beta. Constructs with deleted C-terminal sequences beyond position 114 are designated delta T in FIG. 7 and (1–114) in the table. Thus, for example, LC87 (1–114) contains amino acids 1–87 of human LH beta subunit and amino acids 88–114 of human CG beta. Specific mutations are indicated by the amino acid substituted for that in the native subunit superscripted by the position at which the mutation occurs. Thus, LH thr$^{42}$ indicates the human LH beta subunit which has the methionine at position 42 replaced by threonine. Combinations of alterations in the sequence are correspondingly indicated; for example, LH gly$^{47}$ala$^{51}$ (1–114) is a human beta LH subunit wherein the naturally-occurring amino acids at positions 47 and 51 are replaced by gly and ala respectively, and the portion of LH beta represented by amino acids 115–121 is deleted.

Expression vectors were constructed using pM$^2$ for the illustrative mutants in Table 1 by insertion of the genes into the BamHI site downstream of the LTR promoter. The vectors were then transfected alone or along with pM$^2$/CG alpha (supra) into Chinese hamster ovary cells, as described by Matzuk, M. M., et al., *Proc Natl Acad Sci U.S.A.* (1987) 84:6354–6358; Matzuk, M. M., et al., *J Cell Biol* (1988) 106:1049–1059, both cited above. Successful transformants were selected in 0.25 ug/ml G418, and expression was detected by immunoprecipitation of metabolically labeled cells to select monomer- and dimer-secreting cell lines.

Stably transfected CHO cell lines were maintained in "medium-1" (Ham's F12 medium supplemented with penicillin (100 U/ml), streptomycin (100 ug/ml), and glutamine (2 mM)) containing 5% of v/v fetal calf serum on 0.125 mg/ml G418 in a humidified 5% CO$_2$ incubator.

The cells were plated at 300,000–350,000 cells per well into 12-well dishes in 1 ml medium 1 supplemented with 5% fetal calf serum 1 day prior to labeling. For continuous labeling, cells were washed twice with cysteine-free "medium-2" (medium-1 supplemented with 5% dialyzed calf serum) and labeled for 6 hours in 1 ml of cysteine-free medium 2 containing 20 uCi/ml labeled cysteine. For pulse chase experiments, the cells were washed twice and preincubated for 1.5 hours in cysteine-free medium-2, followed by a 20 minute labeling in cysteine-free medium-2 containing 100 uCi/ml labeled cysteine, then washed twice with medium 2 containing 1 mM unlabeled cysteine and incubated in the unlabeled medium.

The medium and cell lysates were prepared, immunoprecipitated, and treated as described by Corless, C. L., et al., *J Cell Biol* (1987) 104:1173–1181, and in the Matzuk PNAS paper cited above. Antisera against CG beta, LH beta, and the alpha subunit were prepared by standard methods; antisera generated against CG beta cross-reacts fully with LH beta and was used to detect LH beta as well. For characterization of the immunoprecipitates on SDS gels, 15% SDS polyacrylamide gels were soaked for 10 minutes in 1M sodium salicylate, dried, and autoradiographed with preflash film, and scanned, if desired, with an LKB Ultrascan XL laser densitometer.

The effects of the crucial alterations are shown in Table 1.

TABLE 1

Secretion and Assembly of LH Beta-CG Beta Chimeras and Muteins

| Beta Subunit | Monomer | | Dimer | |
|---|---|---|---|---|
| | t1/2 (h) | Recovery+ (%) | t1/2 (h) | Recovery+ (%) |
| CG (beta) | 1.9 | >95 | 1.2 | >95 |
| LH (beta) | 10 | <20 | 5.5 | 42 |
| LHthr$^{15}$* | 7.4 | 40 | 7.7 | 30 |
| LH(1–114) | 7 | 40 | 6 | 80 |
| CG(1–114) | 2.6 | 91 | 2 | 90 |
| LC41 | 5 | 85 | 1 | >95 |
| CL41 | 6.6 | 50 | 2.5 | 50 |
| LC87(1–114) | >10 | 25 | 5.5 | 32 |
| CL87 | 5.3 | 85 | 3 | 45 |
| CL87(1–114) | 2.3 | 95 | 1.6 | >95 |
| CL41(1–114) | 2.5 | >95 | 1 | 94* |
| LHthr$^{15}$(1–114)* | 4.2 | 83 | 3.1> | 95**/40* |
| LHarg$^8$ | >10 | 25 | 5.5 | 32 |
| LHarg$^8$(1–114) | 5.1 | 91 | 2.0 | 91 |
| LHarg$^8$arg$^{10}$(1–114) | 5.2 | 90 | 2.3 | 95 |
| CL41thr$^{15}$(1–114) | 2.5 | >95 | — | — |
| LC41thr$^{15}$ | 4.2 | 91 | — | — |
| LHthr$^{42}$(1–114) | 6.0 | 80 | 2.6 | 84 |
| LHgly$^{47}$ala$^{51}$(1–114) | 7.5 | 28 | — | — |
| LHasn$^{58}$(1–114) | 6.9 | 40 | 2.2 | >95 |
| LHasn$^{77}$(1–114) | 5.7 | 70 | — | — |
| LHtyr$^{82}$ala$^{83}$ | 10 | 50 | — | — |

+For mutants which are slowly secreted, recovery is estimated by comparing the amount secreted and the amount which has disappeared from the lysate in 10 hours.
*Monoglycosylated form recovered in the medium since alpha obscures proper quantitation.
**Recovery of di-glycosylated form is estimated.

As shown in the table, as compared to the behavior of native LH beta, either the deletion of the 7-amino acid C-terminal sequence or a critical single amino acid alteration has some noticeable effect, both on monomer secretion and recovery and on dimer secretion and recovery, but generally the effects are intermediate to a combination of the C-terminal deletion with the appropriate amino acid substitution. Using monomer secretion as a criterion, for example, the t$_½$ decreases dramatically from 10 hours and the recovery increases significantly from a value of less than 20% when the C-terminal deletion is combined with the substitution of the hydrophobic amino acid isoleucine at position 15, of tryptophan at position 8, the methionine at position 42 or the aspartic acid residue at position 77 (although this effect is not as great). Similar results are obtained in assessing the dimer secretion, except that the alteration of the threonine residue at position 58 appears to be very effective in regard to dimerization, while having little impact on the secretion of monomer, and the alteration in the aspartic to asparagine at position 77 appears to have no effect. The data obtained for the chimeras constructed by combinations of LH and CG are consistent with these results.

The modified forms of LH beta of the invention are thus capable of enhanced dimerization with alpha subunit and secretion from the host cell; these modifications to the beta subunit make it possible to produce LH in practical amounts using recombinant host cells. The desirable properties are a result of the deletion or modification of the hydrophobic C-terminus of the beta chain at positions 115–121, in combination with an amino acid modification at a specified location. Any one of the hydrophobic residues at positions 8, 15, and 42 may be replaced by a hydrophilic residue; alternatively, the threonine residue at position 58 may be replaced by asparagine.

Suitable hydrophilic amino acid residues include aspartic, glutamic, glycine, histidine, lysine, asparagine, glutamine, arginine, serine, and threonine. Especially preferred are the neutral hydrophilic amino acids glycine, asparagine, glutamine, serine, and threonine. Especially preferred are replacement of trp at position 8 with arginine and ile at position 15 or met at position 42 with threonine, i.e., with the residue at the corresponding position in CG beta subunit.

With respect to the hydrophobic 7-amino acid sequence at the C-terminus, modification is conveniently made by deletion of the sequence, generally by insertion of a stop codon at position 115 in the gene. Alternatively, the sequence may be replaced by a suitable hydrophilic sequence, most conveniently the 31-amino acid sequence representing the carboxy terminal peptide at positions 115-145 of the human chorionic gonadotropin beta subunit, or a variant thereof.

Of course, additional amino acid modifications which do not interfere with the activity of the LH hormone may also be included. Specifically, modification of amino acids at positions corresponding to amino acid differences between the LH sequence and the CG sequence, whereby the appropriate residue from CG replaces that of LH, are preferred, where such additional substitutions are limited to 1-2 residues.

CARBOXY TERMINAL PEPTIDE MODIFICATION OF OTHER PEPTIDE HORMONES

As described above, the carboxy terminal portion of the CG beta subunit, or a variant of this carboxy terminal peptide, has significant effect on the clearance of CG, FSH and LH. This extension at the carboxy terminus has similar effects on the clearance of other hormones and protein-based pharmaceuticals in general.

Figure 8A:
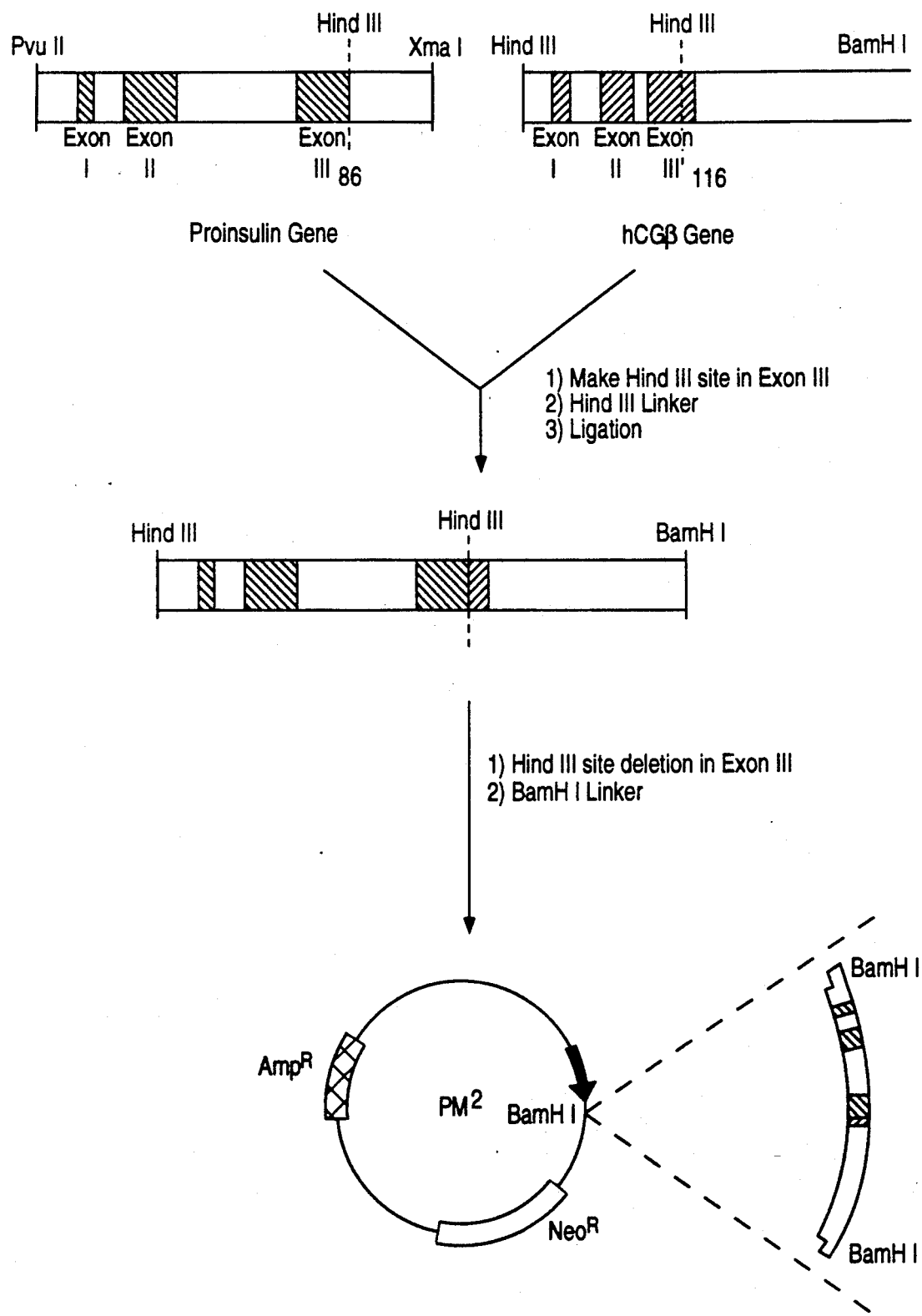
FIG. 8A shows the construction of the gene encoding the extended form of human proinsulin and of an expression vector comprised of that gene; 8B shows the construction of a gene encoding the extended form of human proinsulin and of an expression vector comprised of that gene; 8C shows the construction of a gene encoding the extended form of the alpha subunit of human chorionic gonadotropin hormone and of an expression vector comprised of that gene.
Figure 8B:
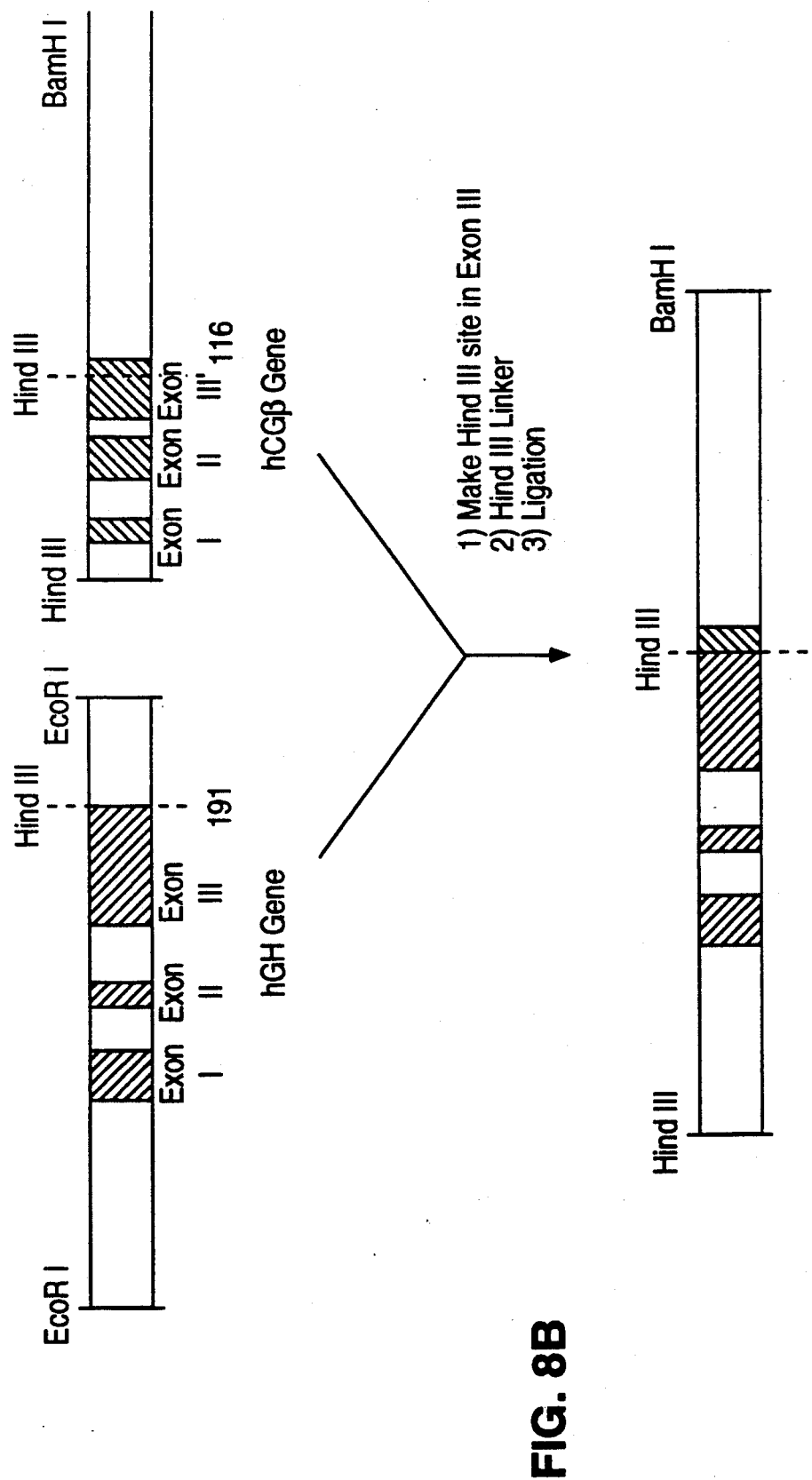
Figure 8C:
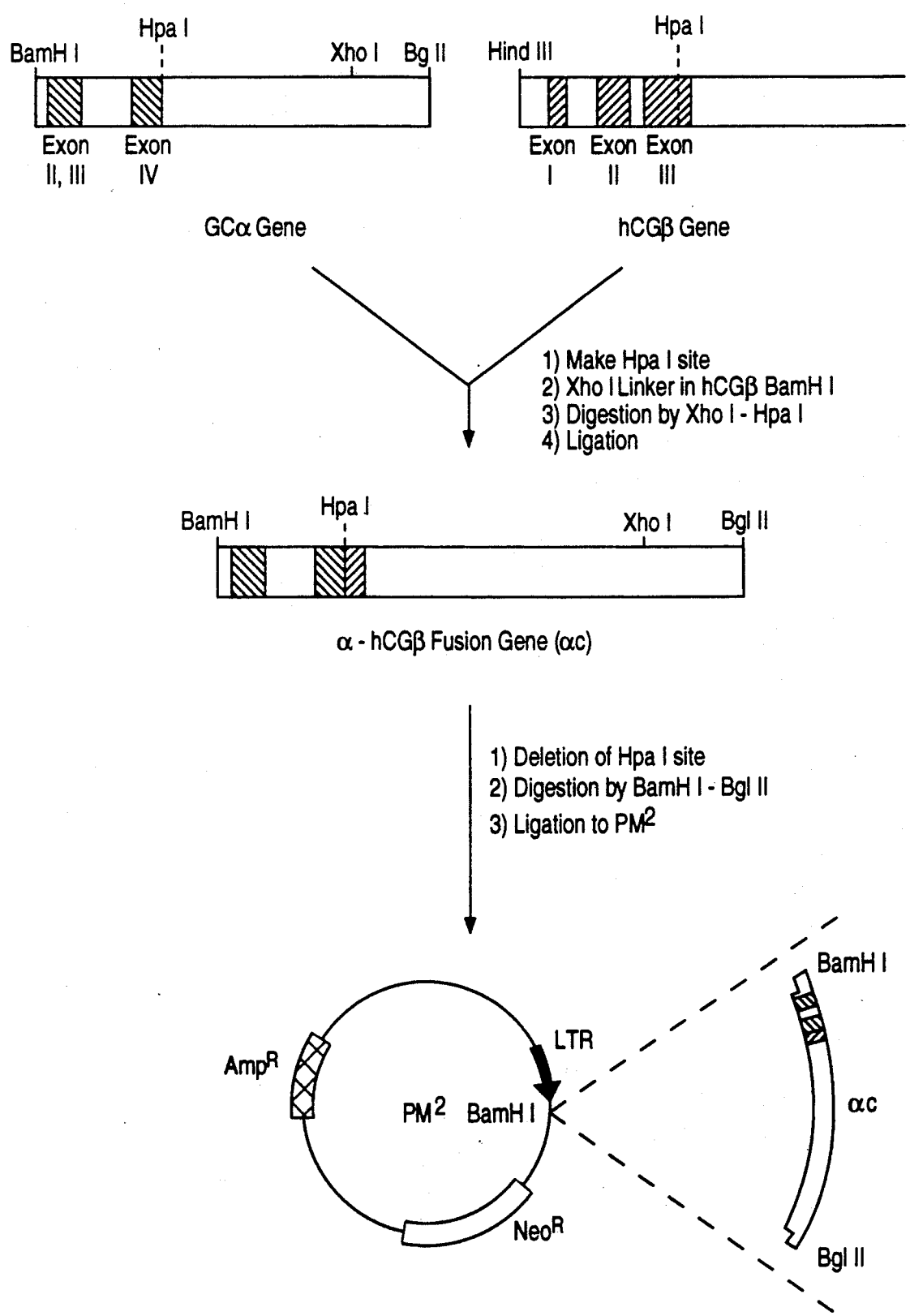

As shown in FIG. 8A, the CTP fragment of hCGβ is ligated to a portion of the PvuII/XmaI DNA fragment encoding the human proinsulin gene as described for the FSHβ subunit gene, supra. The resulting chimeric proinsulin gene can be ligated into the pM2 vector as shown. The same strategy may be used for the modification of human growth hormone (FIG. 8B) or for the α subunit of human gonadotropin (FIG. 8C). As demonstrated above, these modified proteins are expected to have an increased half-life in pharmaceutical applications.

PRODUCTION OF HORMONES WITH GLYCOSYLATION DEFINED BY HOST CHOICE

The expression systems constructed according to the preceding paragraphs can be transfected into a designated host, so that the protein obtained has a glycosylation pattern which is internally consistent within the recovered protein and which is characteristic of the recombinant host employed. This glycosylation may also be optionally modified by changes in the glycosylation sites contained on the amino acid sequence. Recombinant hosts suitable to the expression system constructed must, of course, be employed.

With respect to the illustrated expression system employing the Harvey murine sarcoma virus long terminal repeat, suitable host cells are mammalian, in particular, host cells which are derived from rodents. A particularly preferred host cell, because of convenience and consistency in glycosylation pattern, is a Chinese hamster ovary cell. For the illustrated expression systems, transfectants of CHO cells were obtained by transfection of CHO cells according to the procedure of Matzuk, M. M. et al. (1987), supra, except that the cells were maintained in alpha MEM containing 10% (v/v) bovine calf serum, 100 U/ml penicillin and 100 ug/ml streptomycin as a growth medium. Stable transfectants were selected from this growth medium supplemented with 250 ug/ml G418. Dimer-secreting clones are isolated by screening media and lysates with alpha and beta antisera. The human alpha subunit can be expressed on a separate vector or on the same vector as the beta subunit. For example, pM$^2$/alpha or pM$^2$CG/alpha can be cotransfected with the plasmid containing the beta subunit encoding DNA, or pM$^2$/alpha into which the DNA encoding the beta subunit has been inserted can be used.

By way of illustration, the expression systems described above for human FSH beta inserted into pM$^2$ for expression of FSH beta alone or into pM$^2$/alpha for expression in tandem with the alpha subunit were transfected into CHO cells and stable clones shown to express the beta subunit or dimer were continuously labeled with $^{35}$S-cysteine for 6 hr. The proteins secreted into the media and from cell lysates were immunoprecipitated with appropriate antisera and resolved on SDS-PAGE. The results are shown in FIG. 9 in comparison with the behavior of transformants expressing the gene for human CG beta.

FIG. 9a, which displays gels from 6 hr labeling, shows that in the absence of the alpha subunit, FSH beta is retained in the lysate, while, as shown in FIG. 9b, when the alpha subunit is present, the dimer is formed and efficiently secreted into the medium. The results of experiments wherein the cells are pulse labeled with $^{35}$S-cysteine for 20 min and chased with unlabeled cysteine for up to 12 hr are shown in the remaining segments of FIG. 9. FIG. 9c shows the results for the beta subunit of CG where the lower molecular weight beta subunit in the medium is apparently due to the differences in the extent of glycosylation at the 2 Asn-linked glycosylation sites on CG beta and is unique to this beta subunit. The half-life of CG beta from lysates and of appearance of CG beta in the medium are identical at about 2 hr and almost all the secreted beta subunit can be recovered.

FIG. 9d shows that FSH beta alone is secreted much less efficiently and as does CG beta, disappears from the cell lysates after about 5 hr; less than 20% is recovered in the medium after 12 hr. Similarly to the beta subunits of LH and TSH, FSH beta alone is inefficiently secreted and slowly degraded intracellularly. However, FIG. 9e shows that the presence of the alpha subunit stabilizes and enhances the secretion of the beta subunit for FSH. The half-life for disappearance from the lysates was about 90 min, and 90% was recovered in the medium after 12 hr. This behavior is similar to that shown for TSH above, but different from both CG and LH.

The transformants secreting dimer were tested for biological activity and by chromatofocusing. Rat granulosa cells were treated with increasing aliquots (0.01-1.0 ul/ml) of recombinant FSH-containing medium in an in vitro assay for steroidogenesis as described by Jia, X. C., et al. *J Clin Endocrinol Metab*

Figure 10B:
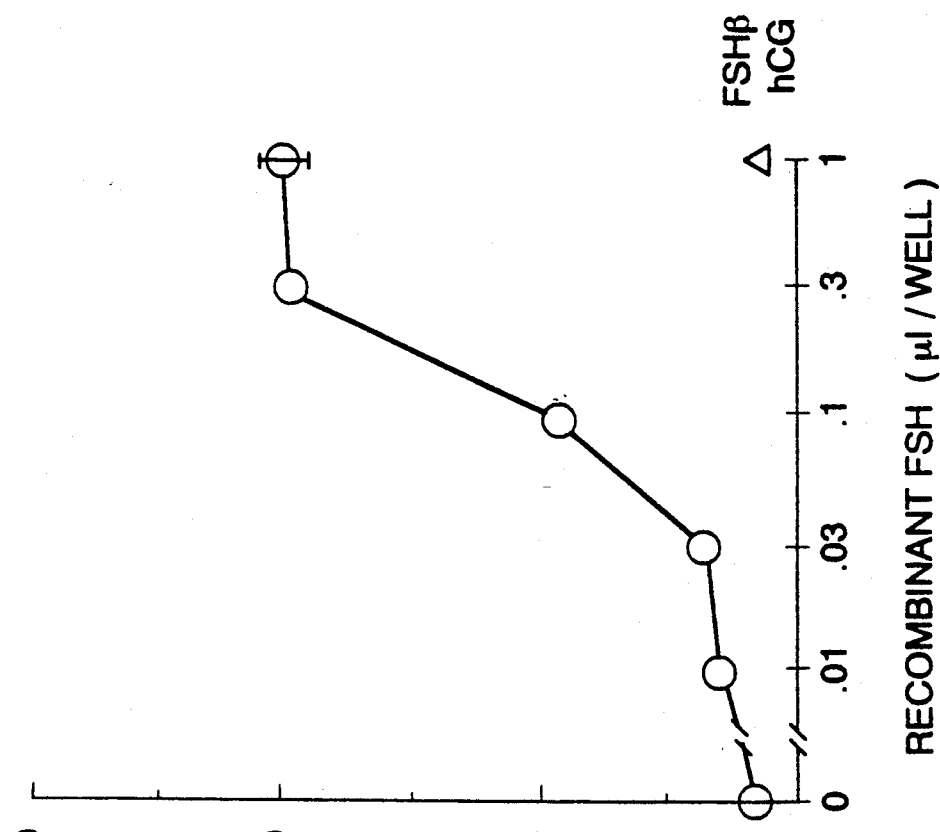
FIG. 10 is a graph showing the results of a bioassay of recombinant human FSH.
Figure 10A:
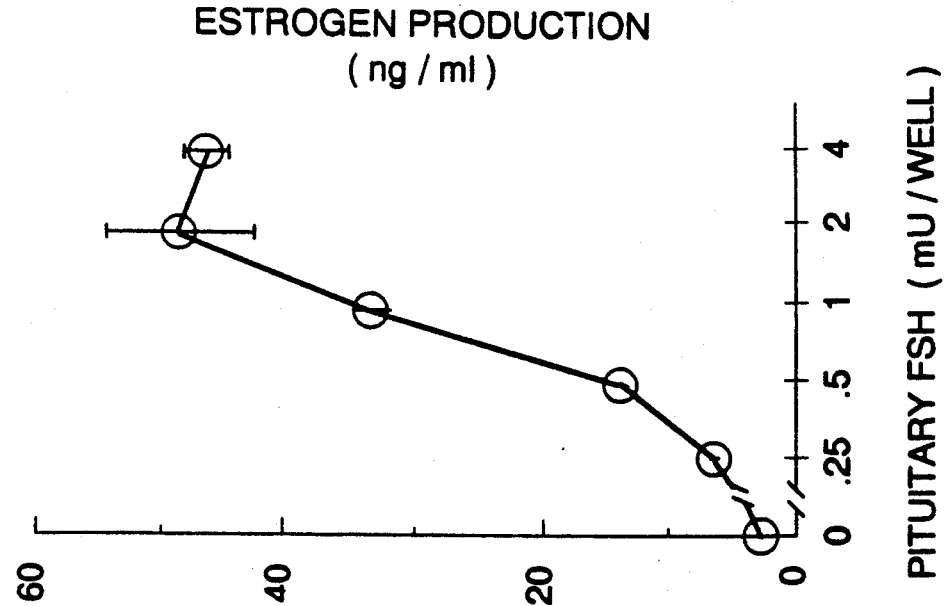

(1986) 621243-1249; Jia, X. C. *Endocrinol* (1986) 119:1570-1577. The results of this assay are shown in FIG. 10. These results show that maximum estrogen production was 10-fold higher than basal values and similar to that induced by pituitary FSH standard LER-907. Neither recombinant CG nor purified FSH beta alone stimulate estrogen production. The results show that the biologically active FSH dimer is secreted at about $1.1 \pm 0.4$ IU/$10^6$ cells/24 hr corresponding to a specific activity of 6600 IU/mg immunoreactive FSH. The cells thus secrete 500 ng FSH/$10^6$ cells in 24 hr.

Figure 11A:
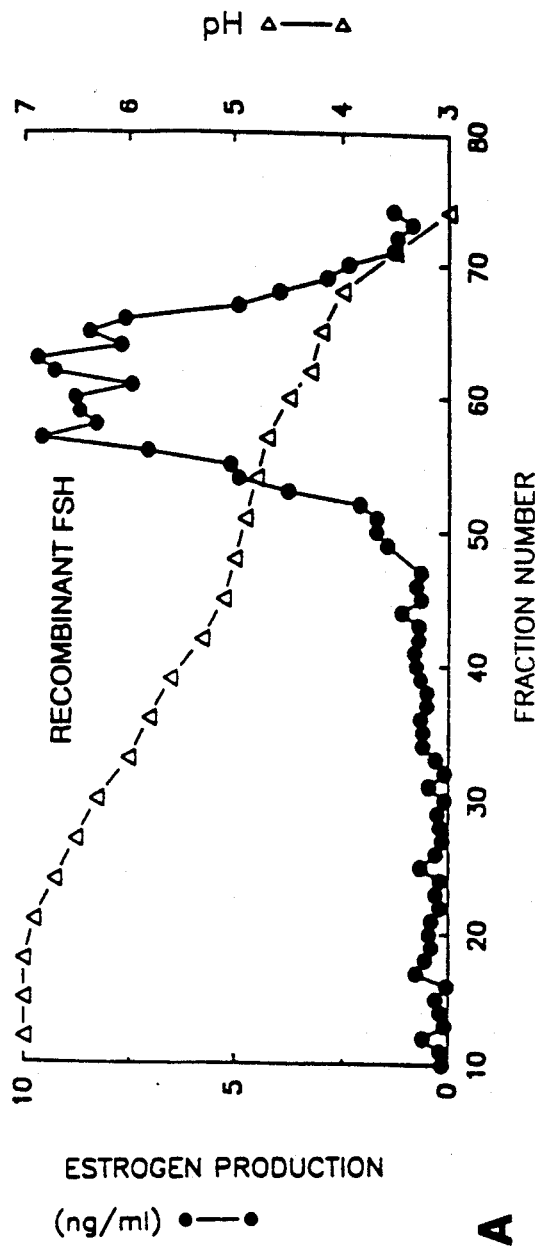
FIG. 11 is a graph showing the results of chromatofocusing of recombinant and pituitary human FSH.
Figure 11B:
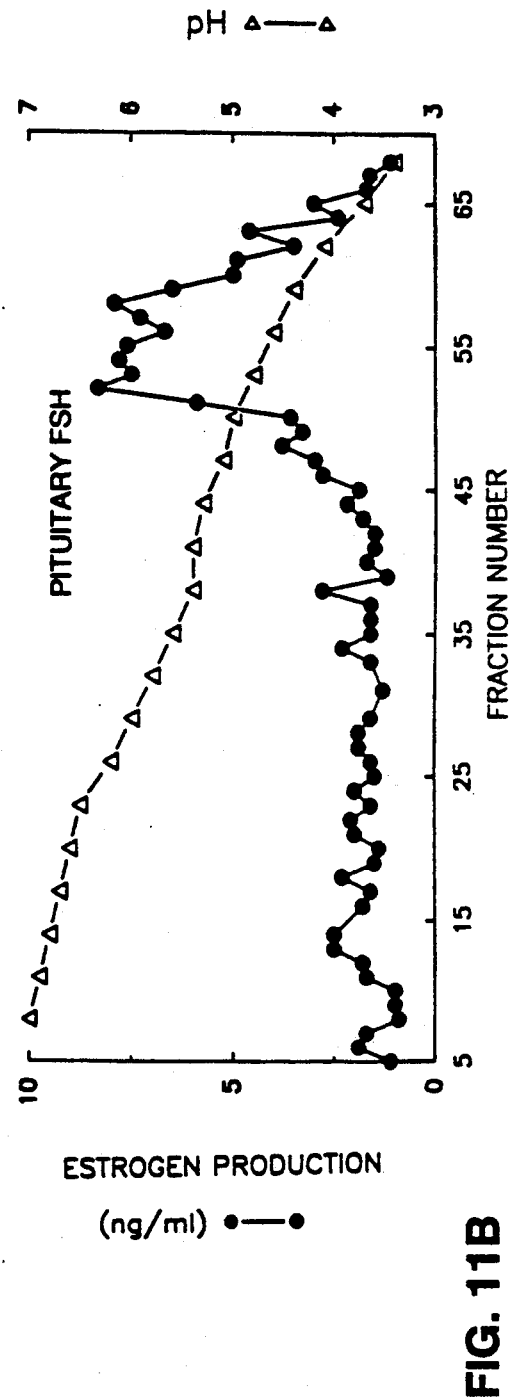

The medium from the transfected CHO cell cultures was chromatographed on a PBE-94 column with a pH gradient from 7.0-3.5 and the FSH bioactivity in each fraction was determined based on the in vitro assay described above. As a control, purified human FSH (NIADD-hFSH-1-3) was treated similarly. The results, shown in FIG. 11, indicate that both recombinant and isolated human FSH show one major peak of activity with pI values between 5.0-3.6 for recombinant FSH and between 5.2 and 3.6 for purified FSH. Pituitary FSH displayed a heterogeneous range of bioactive alkaline forms which was not seen in the recombinant protein. The results from chromatofocusing clearly indicate a uniform nonheterogeneous glycosylated form of the protein.

In addition, a mutant CHO cell line deficient in N-acetyl glucosaminyltransferase I activity, such as 15B, can be used to alter glycosylation in both the alpha and beta subunits of FSH of the heterodimeric hormones. It has been shown that FSH produced in CHO cells deficient in the glycosylation enzyme N-acetyl-glucosamine transferase-1 (NAGT-) results in an Asn-linked (GLcNAc)$_2$ (mannose)$_5$ oligosaccharides. Production of FSH in CHO cells lacking CMP-sialic acid transport into the Golgi apparatus (ST-) results in sialic acid deficient FSH.

INFLUENCE OF GLYCOSYLATION ON SECRETION OF HUMAN ALPHA SUBUNIT

The resultant alpha subunit expression systems constructed as described in the paragraphs above were transfected into CHO cells using a modification of the calcium phosphate method wherein cells were selected for insertion of the plasmid DNA by growing in a culture medium containing 0.25 mg/ml of G418. Resistant colonies were harvested eleven days after transfection and screened for expression of alpha subunit by immunoprecipitation of media or lysates of the cells with the appropriate antiserum. The CHO cells were maintained in Ham's F12 medium supplemented with pen/strep and glutamine (2 mM) containing 5% v/v FCS at 37° C. in a humidified 5% $CO_2$ incubator; transfected clones were maintained with the addition of 0.125 mg/ml G418.

For metabolic labeling, on day 0 the cells were placed into 12 well dishes at 350,000 cells/well in 1 ml medium supplemented with 5% FCS. For continuous labeling experiments, the cells were washed twice with cysteine-free medium supplemented with 5% dialyzed calf serum in place of FCS and were labeled for 7-8 hr in 1 ml of cysteine-free medium containing 5% dialyzed calf serum and 50 uCi/ml $^{35}$S-cysteine (more than 1,000 Ci/mmol). The cell lysates or media were then immunoprecipitated and, if appropriate, treated with endoglycosidases as described by Corless, C. L. et al. *J Cell Biol* (1987) 104:1173-1181. The immunoprecipitates were resolved on 15% SDS polyacrylamide gels.

Using this analysis method, it was clear that the level of glycosylation had an influence not only on the secretion of the alpha subunit, but also on its resultant molecular weight. The results are summarized in Table 2:

TABLE 2

| | Lysate | Medium | % Secreted |
|---|---|---|---|
| alpha WT | 23 kd | 28 kd | >95% |
| alpha(Asn1) or alpha(Thr1) | 20 kd | 22 kd | >95% |
| alpha(Asn2) or alpha(Thr2) | 20 kd | 23.5 kd | <20% |
| alpha(Asn 1 + 2) or alpha(Thr 1 + 2) | 15 kd | 15 kd | ~50% |
| alpha WT + tunicamycin | 15 kd | 15 kd | >95% |

As shown in Table 2, loss of the glycosylation at the position 78 Asn glycosylation site resulted in a substantial decrease in the efficiency of secretion. Evidently additional carbohydrate processing takes place during the secretion which is manifested in the higher molecular weight form found in the medium. This was confirmed by treatment of the secreted forms with endoglycosidaseF which cleaves complex oligosaccharides in addition to high mannose noncomplex and hybrid-type oligosaccharides. More than 95% of the secreted material is sensitive to endoglycosidaseF, but not to endoglycosidaseH which cleaves only high mannose noncomplex and hybrid-type oligosaccharides.

Pulse chase experiments performed as described in Matzuk, M. M. et al. *J Cell Biol* (1988) 106:1049-1059, incorporated herein by reference, shows that the somewhat lower levels of secreted alpha(Asn1) or alpha(Thr1) is due to clonal variation rather than differences in secretion or degradation rates. However, the mutants lacking glycosylation at the second (position 78) glycosylation site showed decreased secretion rates and an increased degradation rate.

It is clear from these results that the glycosylation at position 2 has a profound influence both on secretion rate and on the intracellular stability of the alpha subunit alone.

INFLUENCE OF ALPHA SUBUNIT GLYCOSYLATION ON SECRETION OF hCG

The influence of the glycosylation state of the alpha subunit on the efficiency of assembly of the dimeric hormone hCG was also studied in Matzuk, M. M. (supra).

In the clones wherein hCG beta is formed in excess of the alpha subunit, all of the wild type alpha subunit is mobilized into the dimeric form of the hormone for secretion. On the other hand, those mutants which are missing oligosaccharide from position 52 (glycosylation site 1) are deficient in the secretion of intact hCG dimer by virtue of altering the assembly and/or stability of the dimer complex. However, loss of glycosylation at position 2 seems to have less effect on assembly of the dimeric hormone. Removal of both glycosylation sites has an intermediate effect on assembly; the removal of glycosylation from both sites seems to have a lesser effect on the ability of the hormone to assemble than removal of the glycosylation from position 1 alone. In addition, the beta subunit of hCG stabilizes the mutants at position 2 from degradation of the alpha subunit.

It is clear from the foregoing results that the glycosylation pattern of the alpha subunit determines both the ability of the alpha subunit itself to be secreted and its ability to dimerize with the beta subunit to form intact hormone.

As noted in the paragraph describing the production of alpha subunit muteins, certain designated amino acids in the carboxy-terminal portion of the alpha subunit are required for signal transduction activity. Accordingly, inactivated alpha subunit is useful in the construction of antagonists by dimerization with the appropriate beta subunit of any of the hormones FSH, LH, CG and TSH.

However, it is clear that the influence of the glycoprotein alpha subunit on secretion of beta subunits of the four hormones in this group differs depending on the nature of the beta subunit. Matzuk, M. M., et al. *Molec Endocrinol* (1988) 2:95–100, incorporated herein by reference, show that the presence of the alpha glycoprotein has a different effect on the secretion of human thyrotropin as opposed to human CG or LH. It has been shown that in the absence of the alpha subunit, CG beta is efficiently secreted, but TSH and LH beta subunits are slowly degraded intracellularly and less than 10% secreted into the medium. However, in the presence of the alpha subunit, CG beta is also secreted efficiently as the intact dimeric hormone while only 50% of LH beta appears in the medium as LH dimer. On the other hand, the alpha subunit efficiently combines with TSH beta, since greater than 95% of this beta subunit was secreted as the dimer. This demonstrates that the assembly of the dimeric hormone is dependent on the nature of both subunits.

As described in the paragraphs with regard to the construction of expression systems for FSH beta, mutein forms of FSH beta which are superior in circulating half-life can be produced by construction of a mutein containing the CTP amino acid sequence at the carboxy terminus of human CG beta. In addition, the N-linked glycosylation sites of the FSH beta subunit can be deleted or altered without affecting receptor binding activity.

Mutein forms of hCG are also included in the scope of the invention. Various muteins of hCG containing deleted or altered N-linked glycosylation sites are recombinantly produced by construction of expression systems analogous to those for FSH beta and for the alpha subunit from the suitably modified forms of the appropriate genes. Absence of any or all of the hCG N-linked oligosaccharides had only a minor effect on receptor affinity; with respect to the production of cAMP and steroidogenesis, absence of N-linked oligosaccharides from CG beta or from Asn-78 of the alpha subunit had no effect. However, the oligosaccharide at asparagine-52 of alpha was critical for cAMP and steroid production. In addition, its absence unmasked differences in the two N-linked oligosaccharides present in CG beta and inhibited in vitro biological activity.

EFFECT OF GLYCOSYLATION ON BIOLOGICAL PROPERTIES

It has been demonstrated that complete deglycosylation of human chorionic gonadotropin results in a hormone which retains its ability to bind to receptor, but is no longer capable of effecting the ordinary biological response of the cell on which the receptor is borne. Similar effects of complete deglycosylation are obtained with the additional reproductive hormones LH and FSH. Accordingly, the unglycosylated mutants of the invention, whether obtained through recombinant production in a host which is incapable of such glycosylation, or by mutation so as to eliminate the N-linked glycosylation sites, provides antagonists useful in situations where reproductive function must be regulated and an antagonist is required. Partial deglycosylation as would be obtained, for example, by providing a deglycosylated form of the alpha subunit in combination with a beta subunit, provides molecules with intermediate effects. The alteration of glycosylation sites in the alpha subunit has been described above. Similar alteration of the glycosylation pattern in the beta subunits can be achieved by mutation to eliminate one or both of the glycosylation sites at positions 15 and 30 of the CG beta subunit; one or both of the glycosylation sites at position 7 and 24 of the FSH beta subunit or the glycosylation site at position 30 of the LH beta subunit.

These alternative forms of the hormones can conveniently be produced by the methods of the invention, such as the use of expression systems using the alpha minigene as described above or in combination with the additional modifications of the FSH beta and CG beta subunits, also as described above.

EFFECT OF CTP ON CLEARANCE

The invention further provides a method to improve the clearance characteristics of protein pharmaceuticals and hormones in general by extending their biological half-lives in vivo through a modification which comprises ligation of the carboxy terminal portion of the HCG beta subunit or a variant thereof, as above-defined, to the carboxy terminus of the pharmaceutical or hormone. Such modifications can be made in a manner analogous to that described for the construction of a gene encoding the extended FSH beta subunit above and inclusion of the modified gene in any suitable expression system for production of the protein. Recombinantly produced protein pharmaceuticals are now produced commercially, and accordingly, expression of the modified gene can be effected using commonly known techniques. Suitable candidates for modification include the hormones such as insulin (in which the A subunit would preferably be extended), human growth hormone, bovine growth hormone, tissue plasminogen activator, erythropoietin, various hormone regulators such as LHRH and its analogs, and, in general, any peptide or protein administered for its biological effect. In general, this modification results in an extended half-life, which is advantageous in permitting lower dosages to be used.

UTILITY AND ADMINISTRATION

The hormones and other pharmaceuticals of the present invention are formulated for administration using methods generally understood in the art. Typical formulations and modes of administration are described in *Remington's Pharmaceutical Sciences*, Mack Publishing Co., Easton, Pa., latest edition. These formulations are typically for systemic administration, such as by injection, but oral formulations or topical formulations may also be employed.

The choice of formulation, mode of administration, and dosage level are dependent on the particular hormone or protein and can be optimized for the appropriate indication using generally recognized techniques.

What is claimed is:

1. A modified LH beta subunit having enhanced ability to dimerize with alpha subunit and enhanced secretion as a dimer from mammalian recombinant host cells, as compared to wild-type LH beta subunit, wherein said subunit is a modified wild-type beta subunit wherein the 7-amino acid hydrophobic sequence at positions 115-121 is deleted or replaced by a hydrophilic sequence, and at least one residue selected from the group consisting of trp$^8$, ile$^{15}$, and met$^{42}$ is replaced by a hydrophilic amino acid or thr$^{58}$ is replaced by asn.

2. The beta subunit of claim 1 wherein said residues 115-121 are deleted.

3. The subunit of claim 1 wherein residues 115-121 are replaced by the carboxy terminal peptide (CTP) represented by residues 115-145 of human chorionic gonadotropin (hCG).

4. The subunit of claim 1 wherein the tryptophan residue at position 8 is replaced by an arginine residue.

5. The subunit of claim 1 wherein the isoleucine residue at position at position 15 is replaced by a threonine residue.

6. The subunit of claim 1 wherein the methionine residue at position 42 is replaced by a threonine residue.

7. The subunit of claim 1 wherein the threonine residue at position 58 is replaced by an asparagine residue.

* * * * *

UNITED STATES PATENT AND TRADEMARK OFFICE
CERTIFICATE OF CORRECTION

PATENT NO. : 5,177,193
DATED : 5 January 1993
INVENTOR(S) : Irving Boime and Martin M. Matzuk It is certified that error appears in the above-indentified patent and that said Letters Patent is hereby corrected as shown below:

In Figure 4B, at the end of each line showing amino acid/nucleotide sequence, under "-Ser-Lys" please replace the triplet codes "TGA-GAA" with --TCA-AAG--.

Signed and Sealed this

Twenty-second Day of August, 1995

Attest:

BRUCE LEHMAN

Attesting Officer

Commissioner of Patents and Trademarks